United States Patent
Kim et al.

(10) Patent No.: US 10,010,574 B2
(45) Date of Patent: Jul. 3, 2018

(54) SILK PEPTIDE FOR IMPROVING NEUROPROTECTIVE AND NEUROFUNCTIONAL EFFECTS AND A METHOD OF ITS PREPARATION

(75) Inventors: Sung Su Kim, Gyeonggi-Do (KR); Cheol Hyoung Park, Seoul (KR); Sang-Hyung Lee, Seoul (KR); Wan-Seok Joo, Seoul (KR); Won Bok Lee, Seoul (KR)

(73) Assignee: BRAINGUARD CO., LTD., Seoul (KR)

( * ) Notice: Subject to any disclaimer, the term of this patent is extended or adjusted under 35 U.S.C. 154(b) by 1415 days.

(21) Appl. No.: 11/572,944

(22) PCT Filed: Jul. 31, 2004

(86) PCT No.: PCT/KR2004/001934
§ 371 (c)(1),
(2), (4) Date: Oct. 11, 2007

(87) PCT Pub. No.: WO2006/014033
PCT Pub. Date: Feb. 9, 2006

(65) Prior Publication Data
US 2011/0105402 A1 May 5, 2011

(51) Int. Cl.
*A61P 25/28* (2006.01)
*A61P 25/16* (2006.01)
(Continued)

(52) U.S. Cl.
CPC ...... *A61K 38/011* (2013.01); *C07K 14/43586* (2013.01)

(58) Field of Classification Search
CPC . A61K 38/011; A61K 38/16; C07K 14/43586
(Continued)

(56) References Cited

U.S. PATENT DOCUMENTS 4,324,805 A * 4/1982 Olsen .............................. 426/46
4,898,781 A * 2/1990 Onouchi et al. ......... 428/402.22
(Continued)

FOREIGN PATENT DOCUMENTS

KR 2001-0100728 A 11/2001
KR 2001100728 A * 11/2001
(Continued)

OTHER PUBLICATIONS

Choi et al., Journal of Life Science (Korean Society of Life Science), vol. 10, No. 4, pp. 340-346, 2000 (Abstract Only).*
(Continued)

*Primary Examiner* — Jeffrey Stucker
*Assistant Examiner* — Aurora M Fontainhas
(74) *Attorney, Agent, or Firm* — STIP Law Group, LLC

(57) ABSTRACT

A silk peptide having neuroprotective and neurofunctional activities and its preparation method are discussed. One method relates to preparing silk protein preferably having neuroprotective activity with weight average molecular weight of 200-100,000 by hydrolysis of silk fibroin; also discussed are a composition for preventing or treating brain disease comprising silk peptide and pharmaceutically acceptable carrier, and a composition for improving brain function.

2 Claims, 29 Drawing Sheets

(51) Int. Cl.
*A61K 38/01* (2006.01)
*C07K 14/435* (2006.01)

(58) Field of Classification Search
USPC ........................................................ 514/17.7
See application file for complete search history.

(56) References Cited

U.S. PATENT DOCUMENTS

| 6,372,282 | B1* | 4/2002 | Edens et al. | 426/656 |
| 2002/0028243 | A1* | 3/2002 | Masters | 424/484 |
| 2004/0180027 | A1* | 9/2004 | Kumar et al. | 424/70.14 |
| 2004/0241664 | A1* | 12/2004 | Dekker et al. | 435/6 |
| 2005/0281883 | A1* | 12/2005 | Daniloff et al. | 424/489 |
| 2007/0077333 | A1* | 4/2007 | Maeda et al. | 426/56 |

FOREIGN PATENT DOCUMENTS

| KR | 2003-0077902 A | 10/2003 |
| KR | 2004-0073152 A | 8/2004 |
| WO | 02/076487 | * 10/2002 |

OTHER PUBLICATIONS

Yeo et al., Korean J. Seric. Sci., vol. 46, No. 1, pp. 23-27, Jun. 2004.*
Hess et al., Anal. Biochem., vol. 311, 2002, pp. 19-26.*
Hickey et al., Available and emerging treatments for Parkinson's disease: a review. Drug Design, Development and Therapy 2011:5 241-254.*
Martorelli et al., Effects of Cholinesterase Inhibitors in Cognition on Parkinson's Disease Dementia: A Systematic Review and Meta-Analysis. Advances in Parkinson's Disease, 2015, 4, 90-96.*
Li et al., Enzymatic degradation behavior of porous silk fibroin sheets. Biomaterials 24 (2003) 357-365.*

* cited by examiner

Control Group

Treatment Group

Control Group

BG101 Treatment Group

SILK PEPTIDE FOR IMPROVING NEUROPROTECTIVE AND NEUROFUNCTIONAL EFFECTS AND A METHOD OF ITS PREPARATION

TECHNICAL FIELD

The present invention relates to silk peptide having the effects of neuroprotection and improving brain functions, and a method of its preparation. More particularly, it relates to a method of preparing silk protein preferably having neuroprotective activity with weight average molecular weight of 200-100,000 by hydrolysis of silk fibroin; a composition for preventing or treating brain disease comprising silk peptide and a pharmaceutically acceptable carrier; and a composition for improving brain functions.

RELATED ART

Cerebral apoplexy (or stroke) refers to a cerebral disease, a most highly ranked cause of death in Korea, caused by rupture or obstruction of blood vessels in brain and results in abnormalities in some cerebral tissues. The death rate due to the above disease has been on the rise because of extended life span due to industrialization and development of medical science. Stroke may develop in any part of a body and cause dysfunction of the part accordingly. Medically, stoke is divided into 'ischemic stroke' and 'hemorrhagic stroke', and the former, which is more closely related to hypertension and arteriosclerosis, shows a relatively higher rate of recurrence.

Ischemic stroke is caused by obstruction in from any blood vessel around a neck (e.g. a carotid artery) to any in brain. As a result, cerebral infarction occurs and the function of that region may not be recovered for good. Therefore, the most important thing in treating stroke is prevention of cerebral ischemia itself together with prevention of risk factors such as hypertension, diabetes and elevated level of blood lipid.

Examples of materials currently used for neuronal protection are excitatory amino acid antagonists such as ganglioside and nimodipine, and GABA agonists such as clomethiazole. Magnesium sulfate and glycine antagonist are under $2^{nd}$ phase clinical trial, and a large-scale clinical trial is being performed about piracetam. However, the conventional neuroprotective agents were mainly aimed at acting on each step in ischemia development, and thus still remains a need to develop a composite agent acting on many steps at the same time with little side effects and drug complications. Further, functional food, which may constantly prevent ischemia and inhibit post-ischemic neuronal apoptosis, has been considered to be more effective than the medicine to prevent ischemic stoke itself.

U.S. Pat. No. 6,245,757 discloses a use of progestin for treating cell impairment by ischemia. U.S. Pat. No. 6,380, 193 discloses a pharmaceutical composition comprising poly(adenosine 5'-diphospho-ribose)polymerase inhibitor for treating stroke. Also, U.S. Pat. No. 6,288,041 discloses a pharmaceutical composition comprising sialic acid derivatives for treating stroke.

Parkinson's disease (PD) is one of neuronal degenerative diseases that may cause impairment in movement and intelligence and was first reported by James Parkinson in 1817. In US, the attack rate of this disease is about 100-150 persons per 100,000 people. The number of current patients is about 750,000-1,000,000 and about 60,000 new patients are added to the list each year. Considering the global trend of aging society, its incidence rate is also expected to increase in Korea. Tissue pathologically, PD induces loss of dopamine neuronal cells in substantia nigra and decrease of dopamine in caudate nucleus and putamen, followed by impairment in movement or intelligence such as tremor, bradykinesia, rigidity and disturbance of posture.

Drugs that can supplement functions of dopamine in brain, or prevent or delay destruction of neuronal cells, or control the accompanying symptom such as depression have been used to treat Parkinson's disease. Examples of those drugs are madopar (levodopa, L-dopa; dopamine precursor), bromidine (dopamine receptor agonist), lisuride, artane (anti-acetylcholine) and cogentin. Of these drugs, levodopa is known to be most effective intreating Parkinson's disease by supplementing dopamine concentration in brain. However, when administered for more than 3-5 years, the levodopa shows side effects such as a shortened effective time (wearing-off) or large fluctuation in motion controlling function (on-off phenomenon) and abnormal motion symptom (diskinesia) (Freed et. al., *N. Engl. J. Med.* 327:1549-55(1992)).

Further, surgical treatment for Parkinson's disease has been also used, and its examples are thalamotomy, pallidotomy, deep brain stimulation and Neuronal cell transplantation. However, a lasting time of efficacy differs significantly from patient to patient along with serious side effects such as hypophonia accompanying operation, dysarthria, a decline in memory (Ondo et. al., *Neurology* 50:266-270 (1998); Shannon et. al., *Neurology* 50:434-438(1998)).

Treatment of Alzheimer's disease has been recently focused on the fact that Alzheimer's disease may be caused by impaired cholinergic signaling and transmission in cerebral cortex and hippocampus (Bartus et al., *Science.* 217 (4558): 408-14(1982)); Coyle et al., *Science.* 219(4589): 1184-90(1983)). Because this region in brain is associated with memory and intelligence, functional defect in this region may cause loss of memory and intelligence. Although the process of impairment in neuronal signaling is still controversial, senile plaque and neurofibrillary tangle (NFT) are considered as main causes. Senile plaque due to the accumulation of amyloid β (Aβ) is a notable feature of this disease, and Alzheimer disease may be confirmed by a postmortem examination (Khachaturian, *Arch. Neurol.* 42(11):1097-105(1985)).

As a way of treating Alzheimer's disease, a method of increasing or maintaining acetylcholine amount to inhibit the impairment of cholinergic signaling or causing acetylcholine to acts more effectively on transmission of neuronal cells is provided. Thus, patients of Alzheimer's disease use compounds for increasing activity of acetylcholine. The most effect way is to rapidly decompose acetylcholine in synapse, thus inhibiting activity of acetylcholinesterase, and these inhibitors (e.g. tacrine, donepezil and rivastigmine) are approved by KFDA and currently on market. Despite their effectiveness in preventing further destructive progress of the disease, they are not applied to recover patients to pre-illness level.

Some compounds are aimed to improve neuronal condition and maintain aged cells in good function. For example, NGF or estrogen acts as neuroproting agent to delay neurodegeneration and anti-oxidants decreases cell damage caused by oxidation of cells. Alzheimer's disease becomes serious as amyloid β peptide is accumulated in neuritic space, and amyloid precursor protein (APP) is considered to play a role in combination with proteinase in cells such as α-, β- and γ-secretases. However, the process of amyloid β formation, it is not impossible to control the formation of amyloid β.

It is not certain how the accumulation of amyloid β acts on neuronal transmission. Abnormally cleaved APP induces amyloid β generation, and plaques are induced by the accumulation of the amyloid β. Thus, various factors acting on the cleavage reaction (e.g. inflammation reaction) increase phosphorylation of tau protein, and also increase the accumulation of paired helical filament (PHF) in combination with NFT, resulting in neurodegeneration and finally expedition of dementia of Alzheimer's type.

Up to date, the treatment of Alzheimer's disease is just focused on improvement of the symptom instead of restoring disease process.

U.S. Pat. No. 5,532,219 discloses a pharmaceutical composition comprising 4,4'-diaminodiphenylsulfone for treating Alzheimer's disease. U.S. Pat. No. 5,506,097 discloses a pharmaceutical composition comprising para-amidinophenylmethanesulfonyl fluoride or Ebelactone A for treating Alzheimer's disease. U.S. Pat. No. 6,136,861 discloses a pharmaceutical composition comprising bicyclo[2.2.1]heptane.

Meanwhile, stress is becoming major problem in health in modern society, and it is reported that, in Korea, ⅓ of the twenties usually experience much stress, and that the women suffer from stress than men in their teens. Strength of stress depends on personality, interest, means of relief from stress, surrounding environment, controlling ability of a person, and stress is usually followed by depression. Depression may results in suicide, and is considered to be a very important disorder because of its high rate of occurrence and recurrence. Depression has been reported to be caused by impairment of neurotransmitters such as adrenaline, dopamine or serotonin, and followed by cerebral impairment. Although tricylic antidepression (TAC), especially amitriptyline, is a well known treatment, it has drawbacks of having various side effects. Fluoxetine, a selective serotonin reuptake inhibitor (SSRI) developed in US in 1980's, ranked $7^{th}$ among 20 international drugs because it overcame the problems of TAC and increase the drug compliance. However, SSRI showed little improvement in efficacy compared with TAC and still has serious drug interference.

Further, neuronal disturbance is still induced by stress and there is no way to inhibit the relapse after medicinal treatment of depression, and thus a long-term administration with a lowered dose is only used at present. Therefore, it is very important to develop a material with superior activity of inhibiting neuronal apoptosis and correcting neuronal transmission system. Furthermore, functional foods with anti-depression activity are also important to be developed, as considering a tendency of avoiding visiting treatment institution and overlooking the induction of disturbance in serotonin neuronal system and cerebral impairment.

As representative examples of effort to develop medicine for preventing and treating neuronal degenerative disease, U.S. Pat. No. 6,020,127 discloses genes encoding proteins suppressing neuronal apoptosis from human chromosome 5q13, and U.S. Pat. No. 6,288,089 disclose pyridyl imidazole for treating neuronal degenerative disease by suppressing apoptosis of dopamine neuron.

SUMMARY

Papers and patents are referred to throughout the present specification and references are shown in parentheses. The papers and the patents are incorporated by reference herein in their entirety for better understanding the level of related arts and the gist of the present invention.

The present inventors have performed an intensive research and experiments and finally found that silk peptide produced by hydrolysis of silk protein having a certain range of weight average molecular weight has a superior neuroprotective activity such as prevention or treatment of brain disease and improves various indices for brain function, thus completing the present invention.

Therefore, an object of the present invention is to provide a method of preparing silk peptide having neuroprotective activity.

Another object of the present invention is to provide a pharmaceutical composition for preventing or treating brain disease.

Still another object of the present invention is to provide a food composition for preventing or treating brain disease.

Another object of the present invention is to provide a pharmaceutical composition for improving brain function.

Still another object of the present invention is to provide a functional food composition for improving brain function.

Other objects or advantages of the present invention are better understood by referring to the following Detailed Description and Figures.

DETAILED DESCRIPTION

In one aspect of the present invention, there is provided a method of preparing silk peptide with weight average molecular weight of 200-100,000 having neuroprotective activity by performing hydrolysis of silk protein.

In another aspect of the present invention, there is provided a pharmaceutical composition for preventing or treating brain disease, which comprises (a) a pharmaceutically efficacious amount of silk peptide produced by decomposition of silk protein, and (b) a pharmaceutically acceptable carrier.

In still another aspect of the present invention, there is provided a food composition for preventing or treating brain disease, the composition comprising silk peptide produced by hydrolysis of silk protein as an active ingredient.

In a further aspect of the present invention, there is provided a pharmaceutical composition for improving brain function, which comprises (a) pharmaceutically efficacious amount of silk peptide produced by hydrolysis of silk protein, (b) a pharmaceutically acceptable carrier.

In a still further aspect of the present invention, there is provided a food composition for improving brain function, which comprises silk peptide produced by hydrolysis of silk protein as an active ingredient.

Silk protein is used as a staring material in the present invention. As used herein, the term "Silk" refers to thread produced by silkworm, especially that produced by the larvae of *Bombyx mori* in forming the cocoons within which the worm is enclosed during the pupa stage.

Silk protein consists of about 75% of fibroin and about 25% of sericin, and the silk fibroin and silk sericin are used herein as a raw material of silk peptide. Fibroin protein comprises high amount of glycine and alanine, while sericin has a greater than one third of serine showing a totally different content from that of fibroin. According to recent report, silk fibroin is a huge protein of 2.3 BG101a consisting of H-chain (350 kDa), L-chain (26 kDa) and glycoprotein P25 (30 kDa) with molar ratio 6:6:1, where H-chain forms S—S binding with L-chain and P25 is linked to these chains by non-covalent bonds. Due to this structure, silk fibroin behaves like a polymer having alternating layers of a crystallite region and a non-crystallite region.

In a preferred embodiment, the silk protein is silk fibroin.

In a preferred embodiment, the decomposition of silk protein is accomplished by performing non-limiting reaction selected from the group consisting of (i) decomposition in calcium salt solution, (ii) acid hydrolysis, (iii) hydrolysis by an enzyme, and (iv) a combination thereof. The silk peptide so produced has weight average molecular weight of 200-100,000.

In a more preferred embodiment, the decomposition of silk protein is accomplished by performing (i) decomposition in calcium salt solution, and sequentially (ii) hydrolysis by protease. Further, the decomposition of silk protein is preferred to comprise steps of (a) dissolving silk fibroin in solution comprising calcium salt, (b) removing the calcium salt from the solution, (c) adding mixture of Flavourzyme® and Sumizyme®, whereby producing silk peptide having weight average molecular weight of 200-2,000.

$CaCl_2$.ethanol is usually used as a calcium salt in the decomposition in calcium salt solution (i). The step (a) is preferred to be performed by dissolving silk fibroin in solution comprising calcium chloride, water and ethanol at 60-95° C., more preferably 70-95° C., most preferably 85-90° C. The step (b) may be performed by using various conventional methods such as gel filtration chromatography. The step (d) is preferred to be performed at 45-60° C., more preferably 50-60° C., most preferably at about 55° C. Silk peptide so produced has a relatively high weight average molecular weight of 25,000-50,000, and is not appropriate for food and medication due to its low body's absorption while it is still useful for cosmetics. Silk peptide produced by (ii) acid hydrolysis has weight average molecular weight of 200-10,000. While various acids may be used, a strong inorganic acid is preferred, more preferably hydrochloric acid. The temperature of the reaction (ii) is preferred to be 70-120° C., more preferably 90-110° C. and most preferably 110° C. The reaction (ii) has an advantage that a low molecular weight of peptide is obtained, while it is difficult to appropriately control the range of molecular weight. In one embodiment, the acid hydrolysis (ii) comprises steps of (a) performing hydrolysis in hydrochloric acid solution at 70-120° C., (b) raising pH by adding alkaline solution to the hydrolysis solution, and (c) removing a salt produced in the step (b), thereby producing silk peptide having weight average molecular weight of 200-3,000. Most preferably, silk peptide so produced has weight average molecular weight of 200-1,500. Most appropriate alkaline solution used in the step (b) is sodium hydroxide solution. Various known methods such as gel permeation chromatography may be used as the step (c). Further, peptide produced by acid hydrolysis has substantially 100% solubility in water while it shows very low solubility in organic solvent such as ethanol, methanol, acetone and dimethylformamide.

The aforementioned hydrolysis by an enzyme is performed by using protease. Preferably, the hydrolysis by protease is performed randomly by using a sequence-non-specific protease. The representative example of the protease includes but is not limited to trypsin, pepsin, Alcalase®, Thermoase®, Flavourzyme®, Sumizyme®, Protamex® and protin. In a preferred embodiment, the enzyme used herein is Thermoase®, Flavourzyme®, Sumizyme® or a mixture thereof.

In the case of (iv) the combined reactions, the decomposition of silk fibroin is accomplished by sequentially performing (i) decomposition by calcium salt or hydrolysis by a weak acid or a base and (ii) hydrolysis by an enzyme.

Preferably, the decomposition of silk fibroin is accomplished by sequentially performing (i) decomposition by a calcium salt, and (ii) hydrolysis by Thermoase®, Flavourzyme®, Sumizyme®, and a mixture thereof. The silk peptide so produced has weight average molecular weight of 200-15,000, preferably 200-4,000, more preferably 200-2,000, and most preferably 200-1,200. The silk peptide has substantially 100% solubility in water and shows very low solubility in an organic solvent such as ethanol, methanol, acetone and dimethylamide. In a most preferred embodiment, the decomposition of silk fibroin comprises steps of (a) dissolving silk fibroin in solution comprising calcium salt, (b) removing the calcium salt from the solution, (c) adding a mixture of Flavourzyme® and Sumizyme®.

Preferred peptide herein is (a) one prepared by hydrolysis using silk fibroin as substrate; and (b) one prepared using silk fibroin as substrate by sequentially performing decomposition by calcium salt and decomposition by an enzyme selected from the group consisting of trysin, pepsin, Alcalase®, Thermoase®, Flavourzyme®, Sumizyme® and a mixture thereof. More preferred peptide is (c) one prepared using silk fibroin as substrate by performing decomposition by calcium salt and sequentially decomposition by an enzyme selected from the group consisting of Thermoase®, Flavourzyme®, Sumizyme® and a mixture thereof.

A composition comprising silk peptide herein has an activity in preventing or treating brain disease mainly due to its neuroprotective activity (i.e. protective activity for neuronal cell). As used herein, the term "neuronal cell" includes central nervous system, brain, brainstem, spinal cord, neuron having a structure connecting central nervous system and peripheral nervous system, and neuronal supporting cell, Glia and Schwann cell. As used herein, the term "neuroprotective activity" or "protective activity for neuronal cell" refers to the effect of reducing or ameliorating nervous insult, and protecting or reviving nervous cell that has suffered nervous insult. As used, herein, the term "nervous insult" refers to any damage to neuronal cell or tissue resulting from various causes such as metabolic, toxic, neurotoxic and chemical causes.

Representative examples of disorders, which the composition herein may be applied to, include without limitation neurodegenerative disorder, ischemia-reperfusion injury and mental disorder, and more specifically neurodegenerative disorder such as Alzheimer's disease, Huntington's disease, Parkinson's disease and amyotrophic lateral sclerosis, ischemia-reperfusion injury such as stroke (especially ischemic stroke) and mental disorder such as depression, schizophrenia and post traumatic stress disorder. The composition herein is especially useful for preventing or treating disease due to neuronal damage related to ischemia or reperfusion such as stroke.

The aforementioned effect of the composition herein is mainly due to its neuroprotective activity. The neuroprotective activity may be accomplished via various mechanisms such as inhibition of neuronal cell death, which includes necrosis and apoptosis of neuronal cell. The inhibition of neuronal apoptosis may be accomplished by inhibiting activity of caspase (Guy et. al., *Cell* 91:443-446(1987)), one of targets of silk peptide herein.

The silk peptide herein also has a superior activity for improving brain function or cognitive function. As described in Examples, silk peptide herein remarkably raises various indices in support for improvement of brain function such as memory quotient ('MQ'), learning slope, memory retentiveness, recall efficiency, drawing/memory consensus, language/view consensus, intelligence/memory consensus, short term memory, and attentive concentration.

Silk peptide herein also has a superior activity for improving or preventing damaged brain function due to the brain disease, especially by suppressing the decrease of acetylcholine. Further, the silk peptide herein prevents the damage of brain function by inhibiting neuronal apoptosis. In a preferred embodiment, the brain function is learning capability and/or retentive faculty.

Acetylcholine is neurotransmitter that is projected from basal ganglia to cerebral cortex or hippocampus, thereby performing a very important activity for normal brain function (Richter et. al., *Life Sci.* 19; 26(20):1683-9(1980)). Especially, learning and memory has been known to be varied by drug acting on acetylcholine signaling. Investigation of people who died of Alzheimer type dementia has showed that the major acetylcholinergic neurons are much damaged. Choline agonists and choline esterase inhibitors has been used for patients, as it is recently known that the increase of acetylcholine acts in treating or preventing dementia by improving cognitive function and inhibit the development of dementia. Up to present, there have been developed acetylcholine precursor such as Lecithin; receptor agonist such as RS-86, nicotine and acetylcholine esterase inhibitor such as Tacrine and Aricept, the former of which was approved by KFDA and is on the Korean market and the latter of which was also recently approved by KFDA. However, their use is still open to argument because their effects do not last long, are weak and also seriously toxic, in contrast, silk peptide herein shows negligible toxicity to human body, thus being very useful in medication or food for improving brain function.

As used herein, the term "prevention" or "preventing" refers to inhibiting the generation of disorders or diseases in animal including humans who are not diagnosed to have but are susceptible to such disorders or diseases. As used herein, the term "treatment" or "treating" refers to (a) inhibiting the development of disorders or diseases; or (b) ameliorating or (c) removing the disorders or diseases.

Any pharmaceutically acceptable carriers may be used herein and their representative examples include without limitation carbohydrates (e.g. lactose, amylase, dextrose, sucrose, sorbitol, mannitol, starch and cellulose), acacia rubber, calcium phosphate, alginate, gelatine, calcium silicate, fine crystallite cellulose, polyvinylpyrrolidine, cellulose, water, syrup, salt solution, alcohol, Arabian rubber, vegetable oil (e.g. corn oil, cotton seed oil, soybean oil, olive oil and coconut oil), poly(ethylene glycol), methyl cellulose, methylhydroxy benzoate, propylhydroxy benzoate, talc, magnesium stearate and mineral oil. Pharmaceutical composition herein may further include without limitation a lubricant, a wetting agent, a sweetening agent, flavors, an emulsifying agent, a suspending agent and a stabilizer.

The pharmaceutical composition herein may be orally or parenterally administered, and examples of parenteral administration include intravenous, subcutaneous and intramuscular injection.

Appropriate dosage level of the pharmaceutical composition herein may be determined by considering various information such as formulation method, administration type, age, body weight, sex, physical conditions food, administration time and route, excretion and reaction sensitivity. Physicians with average skill may easily determine and diagnose dosage level of medicine effective for treating or preventing target disorders or diseases. In a preferred embodiment, the dosage level for an adult is once-a-day administration and 0.05-10 g per dose.

The pharmaceutical composition may be prepared in unit dosage form or in multidose container by using pharmaceutically acceptable carriers or fillers according to the conventional method. Representative examples of formulation type include oily or aqueous solution, suspension, emulsion, extract, powder, granule, tablet and capsule, and the formulation may further comprise a dispersing agent or a stabilizer.

Meanwhile, a food composition herein may comprise conventional additives such as protein, carbohydrate, fat, nutrient, and flavor. For example, liquid medicine as an embodiment of the present invention may further comprise citric acid, liquid fructose, sweet, glucose, acetic acid, malic acid, fruit syrup, eucommia bark extract, jujube extract, and glycyrrhiza extract. Considering easy accessibility of food, the food composition herein is very useful in preventing or treating brain disease or oxidative-stress-induced disorders and in improving brain function.

In addition to the aforementioned various activities, the composition herein shows very low side effect to human body compared to medicine prepared by chemical synthesis because the composition herein comprises natural silk peptide as an active ingredient.

The present invention is described more specifically by the following Examples. Examples herein are meant only to illustrate the present invention, but in no way to limit the scope of the claimed invention.

EXAMPLES

Figure 1:
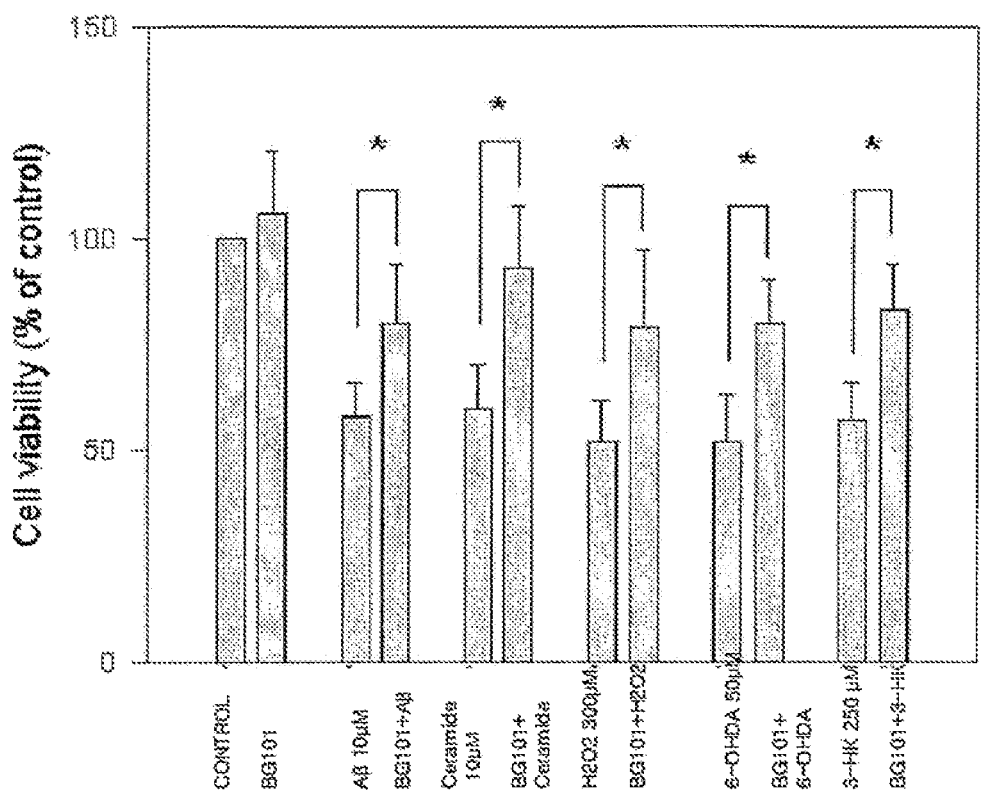
FIG. 1 is a graph showing the result of MIT reduction experimentation to verify the effect of a kind of silk peptide herein on neuronal apoptosis.

Example I: Preparation of Functional Silk Peptide, BG201 and BG101

Example I-1: Preparing Pure Silk Fibroin

Silk protein used herein was prepared by feeding allaged mulberry leaves to *Bombyx mori*. Pupae were removed from cocoons to get rid of sericin. 150 g of cocoons were added into mixture of 8 L of water, 0.45 g of sodium carbonate and 0.75 g of marseillous soap, and the mixture allowed to be boiled for 40 minutes and, this step was repeated twice. The mixture was boiled for 20 minutes by using appropriate amount of water, repeated twice more and washed three times and dried, thus allowing sericin to be solved off. The reduced mass was 37 g (25% reduced), and pure silk fibroin was prepared by washing and drying the mixture.

Example I-2: Preparation of Silk Peptide BG101

35 g of fibroin prepared in Example I-1 was added into solution comprising calcium chloride ($CaCl_2$, 1.sup.st grade, Mw=110.99), $H_2O$ and ethanol with a molar ratio of 1:8:2, and dissolved at 90° C. for 5 hours. The mixture was filtered to remove impurities by using gauze and non-woven fabric, and diluted by adding the same amount of distilled water. Neutral salt was removed by using gel chromatography device with 10 cm of diameter and 1 m of length (GradiFac system, Pharmacia Biotech, Sephadex G-25 Media, HiLoad P-50 Pump UV-1 Monitor, Sweden). To the prepared fibroin solution, 1% of one out of the following combination of proteases were added and hydrolysis was performed at 55° C. for 5 hours: (1) 1:1 of Flavourzyme® and Sumizyme® (NOVA, US), (2) 1:1 of trypsin and pepsin, (3) 1:1 of Thermoase® Alcalase®. The mixture was thermally treated at 100° C. for 5-10 minutes to remove the activity of enzyme, and cooled dried, thus obtaining powders named "BG101".

Example I-3: Preparation of Silk Peptide BG201

113 g of fibroin prepared in Example I-1 was added to 3,400 mL of chloric acid solution (25%), and hydrolysis was performed at 110° C. for 12 hours, followed by addition of sodium hydroxide solution (4 M) to maintain pH to 5.0-5.5. The solution was paper-filtered and passed through filter filled with activated carbon, followed by electrolytic desalting process by using an electro-dialysis device that automatically control current and voltage to 20 mA and 15 V, respectively. Powders were prepared by using a spray drier and named as "BG201".

Example II: Analysis of Silk Peptide

Example II-1: Molecular Weight

Absolute molecular weights of BG101 and BG201 were determined by using gel filtration chromatography method. Particularly, the concentration of the sample was controlled within 0.5% by using 0.2 N $NaNO_3$ solution as buffer solution, and property data of the sample were obtained such as refractive index (RI), light scattering (LS), diffraction pressure, UV adsorption (280 nm). GPC system (Viscotec, US) was used that automatically calculates the absolute molecular weight distribution from the data. As a standard, polyethylene oxide (PEO, $M_w$=110,000) was used for verifying reproducibility, and weight average molecular weights of BG101 and BG201 were verified as 1070 and 850, respectively.

Example II-2: Solubility in Various Solvents 0.1 g of silk peptide powders were dissolved in 10 mL of distilled water, ethanol, methanol, acetone and dimethyl formamide and solubilities (%) of BG101 and BG201 in those solvents were measured, as shown in Table 1. BG101 and BG201 were verified to be fully soluble in distilled water while the solubilities in organic solvents such as ethanol and methanol were drastically decreased.

TABLE 1

| Solvents | Distilled water | Ethanol | Methanol | Acetone | Dimethyl formamide |
|---|---|---|---|---|---|
| BG101 | 100 | 20 | 45 | 30 | 50 |
| BG201 | 100 | 30 | 50 | 32 | 50 |

Example II-3: Solubility at Various pH Values 0.1 g of silk peptide powders were dissolved in 10 mL of distilled water. Solubilities at pH 3, 5, 7, 9 and 11 were measured and pH was controlled by using 0.1 N of hydrochloric acid and sodium hydroxide. As shown in Table 2, silk peptide was verified to be fully soluble irrespectively of pH value of solvents.

TABLE 2

| pH | 3 | 5 | 7 | 9 | 11 |
|---|---|---|---|---|---|
| BG101 | 100 | 100 | 100 | 100 | 100 |
| BG201 | 100 | 100 | 100 | 100 | 100 |

Example II-4: Amounts of Amino Acids

Compositional analysis was performed to determine the amounts of amino acids in BG101 and BG201, respectively. 0.05% of each sample was added in 1 mL of chloric acid solution and nitrogen treatment was performed, followed by hydrolysis for 18 hours at 110° C. The solution was totally evaporated off hydrochloric acid and diluted with loading buffer solution of pH 2.2. Compositional analysis on amino acid was performed by using automatic amino acid device (Biochrom 20 Plus, Sweden) and the results were provided in Table 3.

TABLE 3

| Amino acid | BG201 | BG101 |
|---|---|---|
| Gly | 43.2 | 42.46 |
| Ala | 27.2 | 26.64 |
| Ser | 15.94 | 11.24 |
| Tyr | 2 | 4.41 |
| Val | — | 2.02 |
| Asp | 1.45 | 2.11 |
| Glu | 1.61 | 1.68 |
| Thr | 0.6 | — |
| Met | 0.15 | 0.11 |
| Ile | 0.98 | 0.65 |
| Leu | 0.71 | 0.57 |
| Phe | 1 | 0.76 |
| His | 0.52 | 0.52 |
| Lys | 0.38 | 1.04 |
| Arg | 1.01 | 1.04 |
| Total | 96.21 | 95.25 |

As shown in Table 3 above, BG101 and BG201 are similar to each other in the contents of amino acids, while they showed noticeable difference in their in vivo or in vitro activities, which means that the resultant silk peptides have different structures depending on their preparation methods.

Experimental Example I: Verification of Neuroprotective Activity and Anti-Oxidative Function Experiments set forth below were performed to verify the effect of silk peptide on neuronal cells.

Experimental Example I-1: Selection of Neuronal Cells and Culture of Cells

Pure neuronal cells were prepared by performing primary culture of neuronal cells according to Okuda's method (Okuda S. et al., *Neuroscience* 63(3):691-9(1994). Particularly, striatum was prepared from 15 day embryo of a mouse (E15) and each cell was separated by treatment of 0.25% trypsin and 0.01% DNase I, and further separated with pipette. Each cell was placed on PEI coating plate at a density of $1\times10^5$ cells/cm$^2$, and culture of neuroglial cell was inhibited by using ara-C. Further, neuron-derived cell lines, SK-N-SH or SHS-Y5Y (ATCC, US) were placed on PEI-coating plate at a density of 80% and culture by using culture solution comprising DMEM or RPMI and 10% of FBS. As set forth in the following Experimental Examples, pretreatment was performed by using low-serum medium (1% FBS contained) before treatment of amyloid β(Aβ), 6-hydroxydopamine (6-OHDA), ceramide, $H_2O_2$ or 3-hydroxykynurenine (3-HK).

Experimental Example I-2: MIT Reduction Experiments (Verification of Cell Survival)

To verify the effect of BG101 and BG201 on apoptosis of neuronal cells, MTT reduction experiment was performed by modifying a known method (Shearman et al., *Proc. Natl. Acad. Sci.* 91(4):1470-4(1994), Shearman et al., *J. Neurochem.* 65(1):218-27(1995), and Kaneko et al., *J. Neurochem.* 65(6):2585-93(1995)) as follows. Neuronal cells, which were selected and cultivated in the Experimental Example above, were treated with 10 pM BG101 or BG201 for 6 hours with, followed by addition of 10 μM Aβ, 10 μM 6-OHDA, 10 μM ceramide, 300 μM $H_2O_2$, or 250 μM 3-HK. The added materials induced about 50% apoptosis within 36 hours due to the cellular cytotoxicity.

The samples were incubated in 5% $CO_2$ at 37° C. for 48 hours, followed by further culture for 4.5 hours after addition of 3-(4,5dimeylthiazol-2-yl)-2,5-diphenyltetrazolium bromide (MIT: Sigma, US) solution to the concentration of 0.5 mg/mL.

Figure 2:
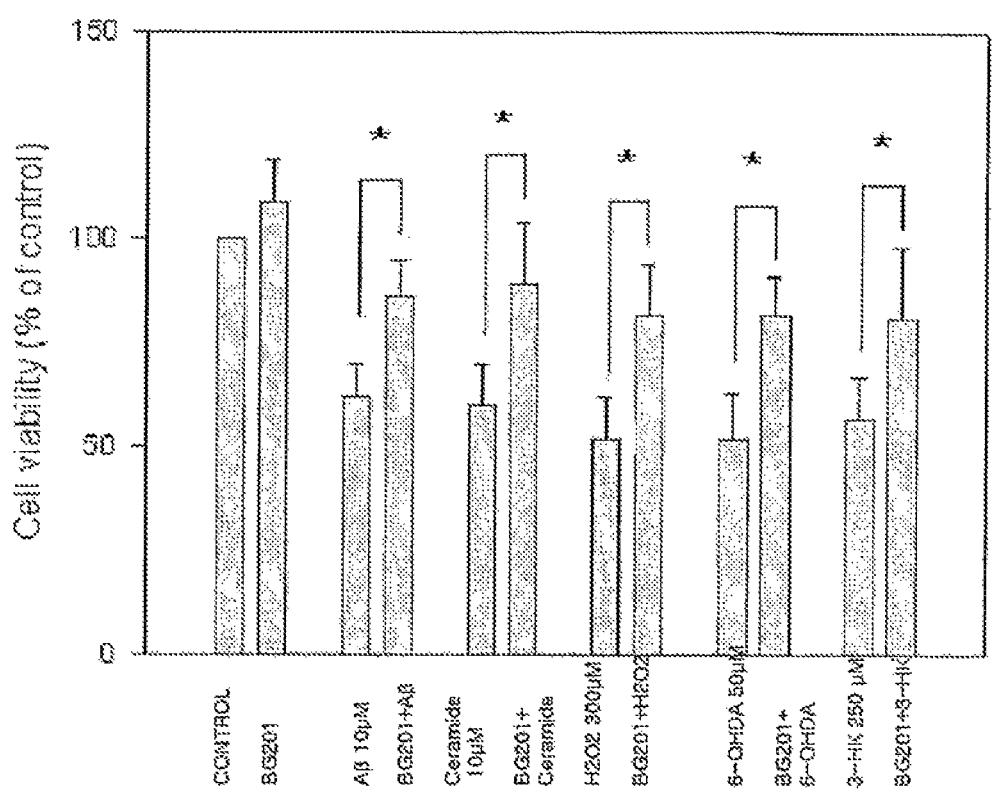
FIG. 2 is a graph showing the result of MIT reduction experimentation to verify the effect of another kind of silk peptide herein on neuronal apoptosis.

Formazan precipitates formed by MTT reduction were dissolved in the solution (0.1 N HCl in anhydrous isopropanol), and absorbance at 570 nm was determined by using ELISA Reader (Molecular Devices, US). As shown in FIGS. 1 & 2, a value of each sample was determined by selecting appropriate value between cell viability of 100% (control group, only solvent used) and cell viability of 0% (cells are totally destroyed by 0.9% of Triton X-100. The values in FIGS. 1 & 2 are expressed as 'mean±standard deviation'. BG101 and BG201 were verified to be effective in inhibiting neuronal apoptosis ($P<0.05$).

Meanwhile, to check the aforementioned results, cell viability was further determined as 'surviving cells/total cells' by staining with tryphan blue or crystal violet to measure the each number of total cells and apoptotic cells with hematocytometer. The obtained results were verified to be very similar to the aforementioned results. Further, it was verified that cell death occurs in the form of apoptosis, which was also confirmed by the observation of DNA degradation after Hoechst staining.

Experimental Example I-3: Hoechst Staining

Figure 3:
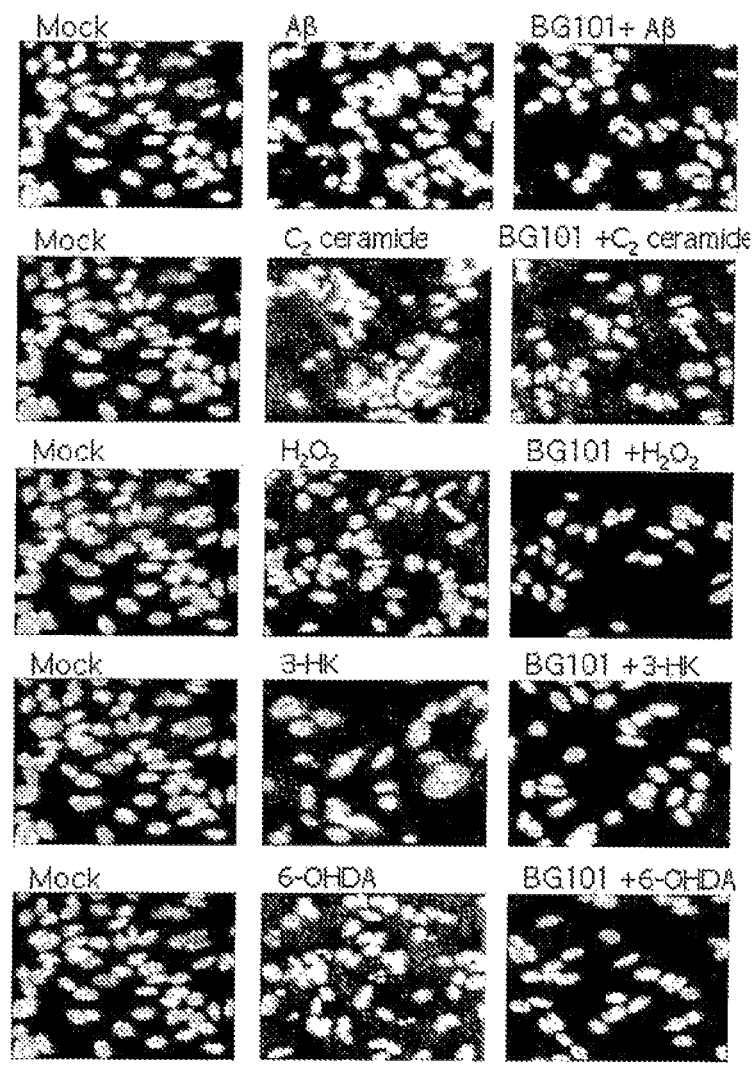
FIG. 3 is the result of Hoechst staining experiment and shows that a kind of silk peptide herein inhibits neuronal apoptosis.
Figure 4:
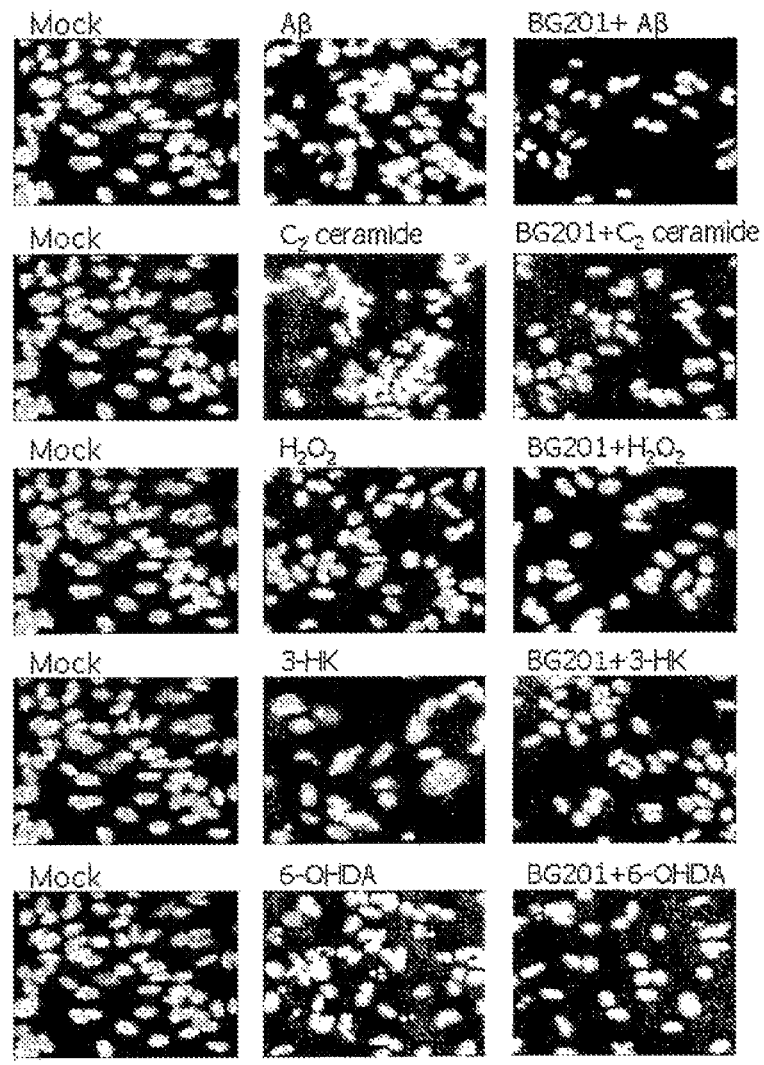
FIG. 4 is the result of Hoechst staining experiment and shows that another kind of silk peptide herein inhibits neuronal apoptosis.

As set forth in Experimental Example I-2, neuronal cells were treated with BG101 or BG201 for 6 hours with and cultivated, followed by addition of 10 μM Aβ, 10 μM 6-OHDA, 10 μM ceramide, 300 μM $H_2O_2$, or 250 μM 3-HK. The cells were fixed with 4% paraformaldehyde (in PBS, pH 7.4) for 15 min and washed with BPS, followed by staining with 8 μg/ml of Hoechst dye 33258 solution (Sigma, US) for 5 min. They were washed twice with distilled water and mounted with glycerol:PBS mixture (9:1), and analyzed under fluorescent microscope (Olympus microscope, Japan), as shown in FIGS. 3 & 4. The cells, which were treated only with apoptosis inducing agent, showed a typical apoptosis morphology such as chromatin condensation and nuclear fragmentation, which was effectively inhibited by pretreatment of BG101 and BG201 followed by insult treatment. Mock referring to control group shows normal nuclear morphology. As shown in FIG. 2, BG101 and BG201 herein were verified to be effective in suppressing apoptosis, which confirms the reliability of the aforementioned Experimental Example I-2.

Experimental Example I-4: Caspase Activity Experiment

Figure 5:
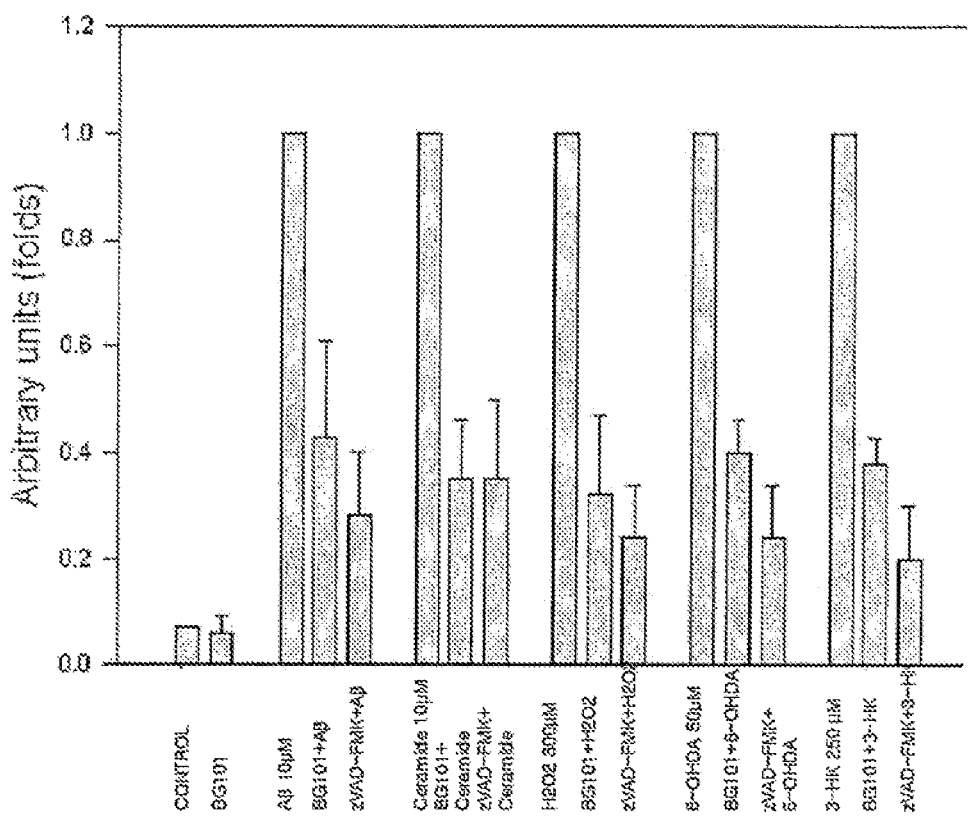
FIG. 5 is a graph showing that a kind of silk peptide herein inhibits the activity of caspase.
Figure 6:
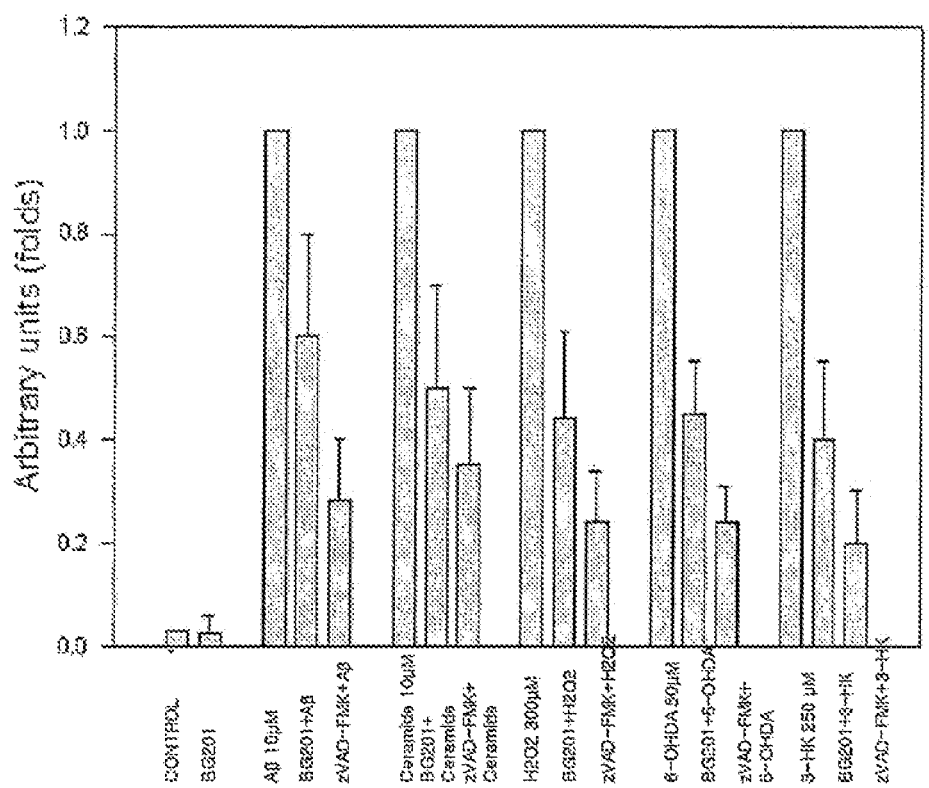
FIG. 6 is a graph showing that another kind of silk peptide herein inhibits the activity of caspase.

The following experiments were performed to verify that the inhibition of apoptosis was due to the inhibition of caspase activity. As set forth in Experimental Example I-2, neuronal cells were treated with BG101 or BG201 for 6 hours with and incubated, followed by addition of 10 μM Aβ, 10 μM 6-OHDA, 10 μM ceramide, 300 μM $H_2O_2$, or 250 μM 3-HK. Cell-dissolved solution was obtained by destroying $10 \times 10^6$ cells per P100 plate with cell-dissolving buffer solution (50 mM Tris-Hcl, 0.03% IGEPAL, 1 mM DTT, pH 7.5). 500 μM of Ac-DEVD-AMC (Enzyme Systems Products, Canada), fluorescence producing substrate of caspase, which was prepared from HEPES buffer solution (40 mM HEPES, pH 7.5, 20% glycerol, 4 mM DTT) was added in 50 μL of the cell-dissolved solution, and reaction was performed at 37° C. for 1 hour. A positive control was prepared by pretreating 10 μM of zVAD-FMK (Enzyme Systems Products, ESP, Canada), pan-caspase inhibitor. The degree of fluorescence that was emitted when the substrate was cleavaged by caspase was measured by using fluorescence analyzer (Perkin-Elmer Luminometer; excitation wavelength 380 nm, emission wavelength 420-460 nm). To quantify the measured fluorescence, standard curve was prepared by using degree of fluorescence of cleavaged FMK (FIGS. 5 & 6; P<0.05). As shown in FIGS. 5 & 6, BG101 or BG201 herein is verified to inhibit the caspase activity that is caused by an apoptosis-inducing agent. Thus, it can be concluded that apoptosis inhibition effect of BG101 and BG201 is related to the inhibition of caspase activity.

Experimental Example I-5: Quantitative Determination of Reactive Oxygen within Cells Reactive oxygen is a main reason of aging and also directly or indirectly causes many kinds of disease. Thus, the present invention investigates the effect of silk peptide herein on the reactive oxygen.

As set forth in Experimental Example I-2, cells were treated with BG101 or BG201 for 6 hours with and cultivated, followed by addition of 10 μM Aβ, 10 μM 6-OHDA, 10 μM ceramide, 300 μM $H_2O_2$, or 250 μM $FeSO_4$ or 3-HK. The cultivated cells were treated with 10 μM [2] DCFDA (6-carboxy-2',7'-dichloro-dihydrofluoresceine diacetate, dicarboxym-ethylester) dissolved in HCSS buffer solution (20 mM HEPES, 2.3 mM $CaCl_2$, 120 mM NaCl, 10 mM NaOH, 5 mM KCl, 1.6 mM $MgCl_2$, 15 mM glucose) and 2% of pluronic F-127, suspension supplementer, at 37° C. for 30 minutes. DCF fluorescence by reactive oxygen in cells was observed at room temperature by using Olympus IX70 equipped with mercury lamp fluorescence attachment (excitation wavelength 488 nm, emission wavelength 510 nm), and the screen was captured by CCD camera and analyzed by using NIH Image 1.65 program (FIGS. 7 & 8).

Figure 7:
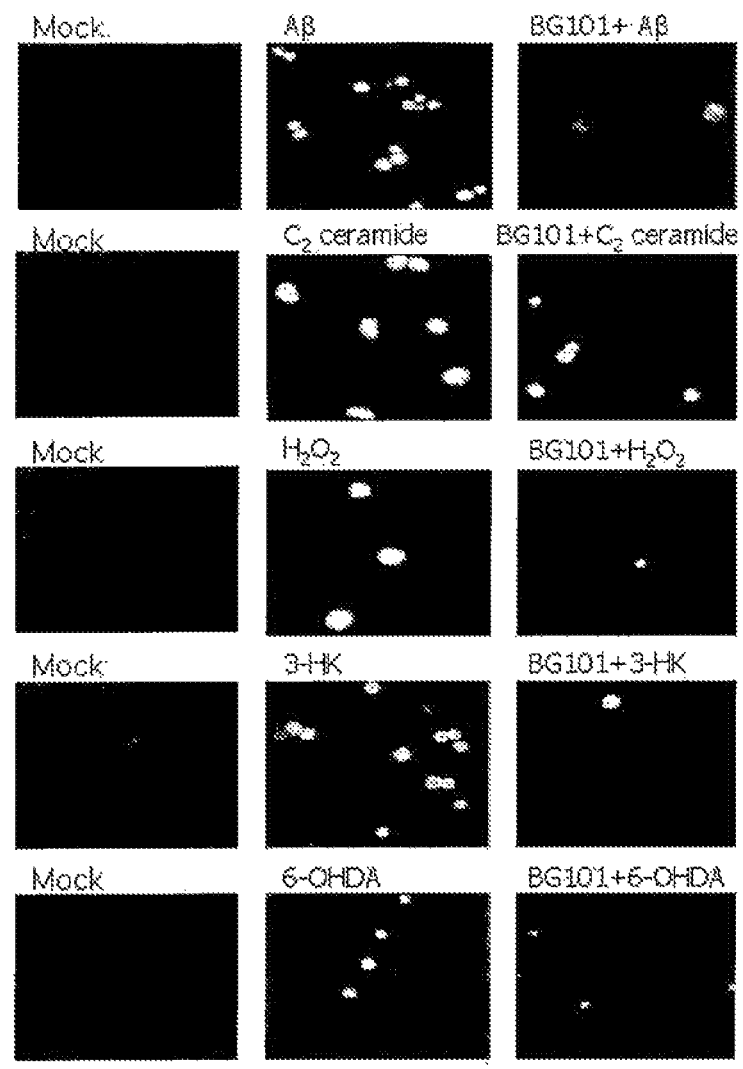
FIG. 7 is a photograph showing that a kind of silk peptide herein inhibits the generation of reactive oxygen in cells.
Figure 8:
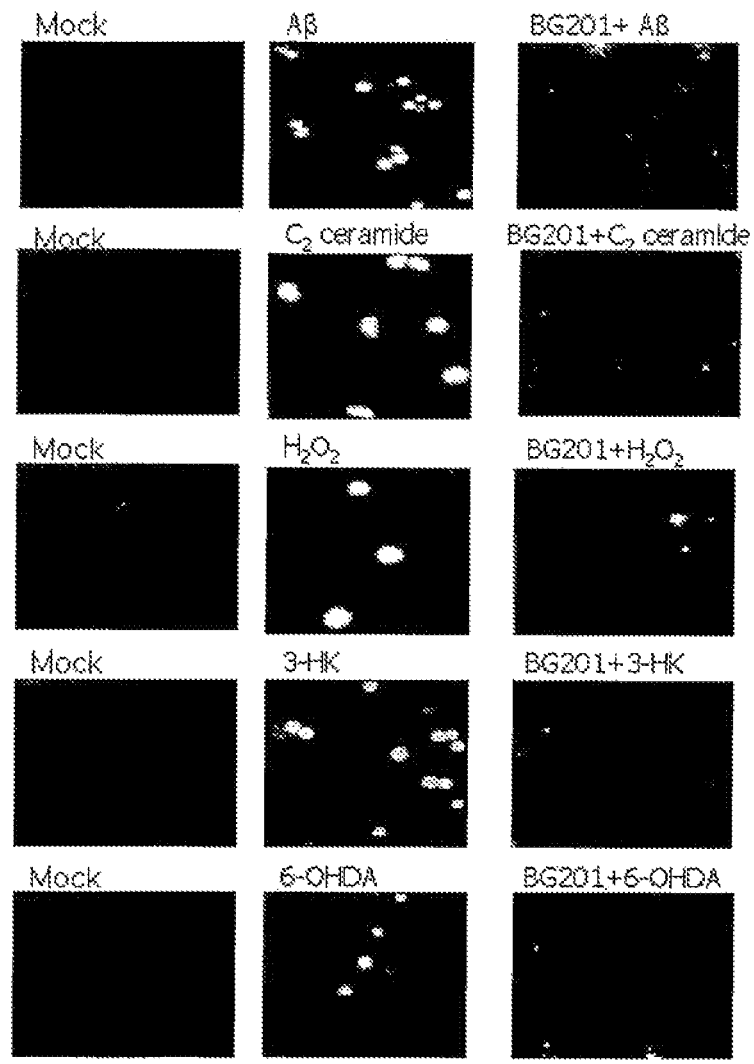
FIG. 8 is a photograph showing that another kind of silk peptide herein inhibits the generation of reactive oxygen in cells.

Mock in FIGS. 7 & 8 refer to specimen treated only with a solvent. Reactive oxygen was verified to generate by treatment of Aβ, 6-OHDA, ceramide, $H_2O_2$, $FeSO_4$ or 3-HK (FIG. 4), while the pretreatment of BG101 or BG201 remarkably inhibited the reactive oxygen generated by an apoptosis-inducing agent.

Therefore, it can be concluded that BG101 or ED has an anti-oxidative activity by inhibiting generation of reactive oxygen induced by amyloid β, 6-OHDA, ceramide, $H_2O_2$, $FeSO_4$ or 3-HK.

Experimental Example II: Ischemic Animal Model Experiment

The following experiments were performed to investigate the effect of silk peptide BG101 or BG201 herein on the area of ischemic infaction.

Experimental Example II-1: Local Ischemia Induced Animal Model

A. Medicine Treatment and Preparation of Local Ischemia Induced Animal Model

Local ischemia induced, animal model was prepared by using male Sprague-Dawley rat (200-250 g). Vehicle treated group (n=6) were orally administered with 1 g/Kg of BG101 1 hour before or after ischemia induction, and vehicle control group (n=6) were administered with the same amount of a saline solution. The test subject animals were administered with 30-40 mg/Kg of ketamine by intramuscular injection and anesthetized. Common carotid artery, external carotid artery and internal carotid artery were separated. Superior parathyroid gland and posterior fossa, which are branches of the external carotid artery, and pterygopalatine, which is a branch of the internal carotid artery, were electrocauterized, and the external carotid artery were cut. Occlusion of origin of middle cerebral artery was performed by incorporating 4-0 nylon thread (ETHICON, INC, US) into the internal carotid artery through the external carotid artery, and placing 10-48 mm of nylon thread within the common carotid artery.

B. Decrease in Area of Ischemic Infarction

Brains were dissected from the animal 6 hours after induction of ischemia. The dissected brains were cut at interval of 2 mm from anterior pole, and reacted with 2% triphenyl tetrazolium chloride (TTC, Sigma, US) at 37° C. for 30 minutes, followed by fixing using 4% paraformaldehyde (Sigma, US). Tissue parts were photographed (FIGS. 9 & 12) and areas of red-stained normal region and white infarction regions were measured by using MCID image processing system (Imaging Research Inc., Canada), thereby calculating the average ratio of the areas (FIG. 10).

Figure 9:
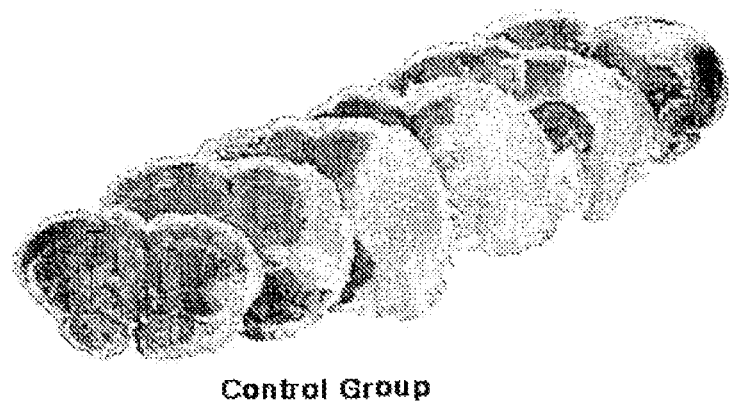
FIG. 9 is a photograph showing the effect of silk peptide herein on the parts of ischemic cerebral infarction.
Figure 9:
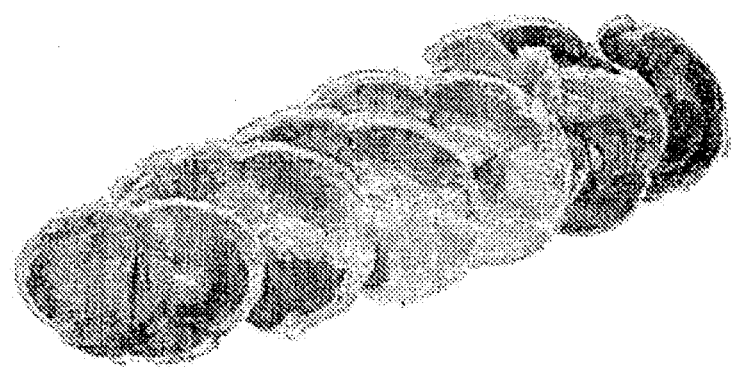
Figure 10:
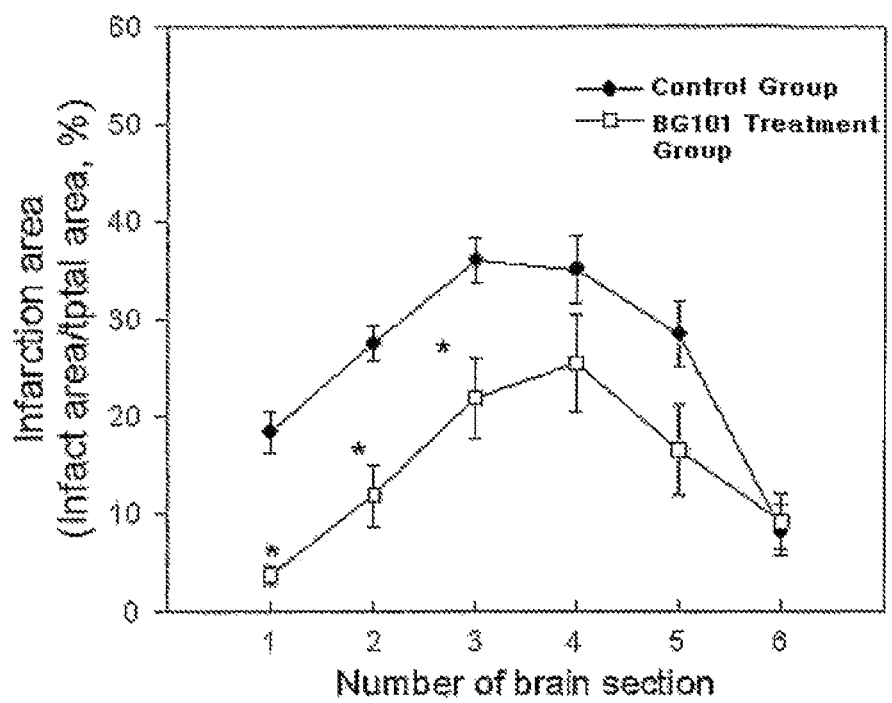
FIG. 10 is a graph showing the effect of silk peptide herein on parts of ischemic cerebral infarction.
Figure 11:
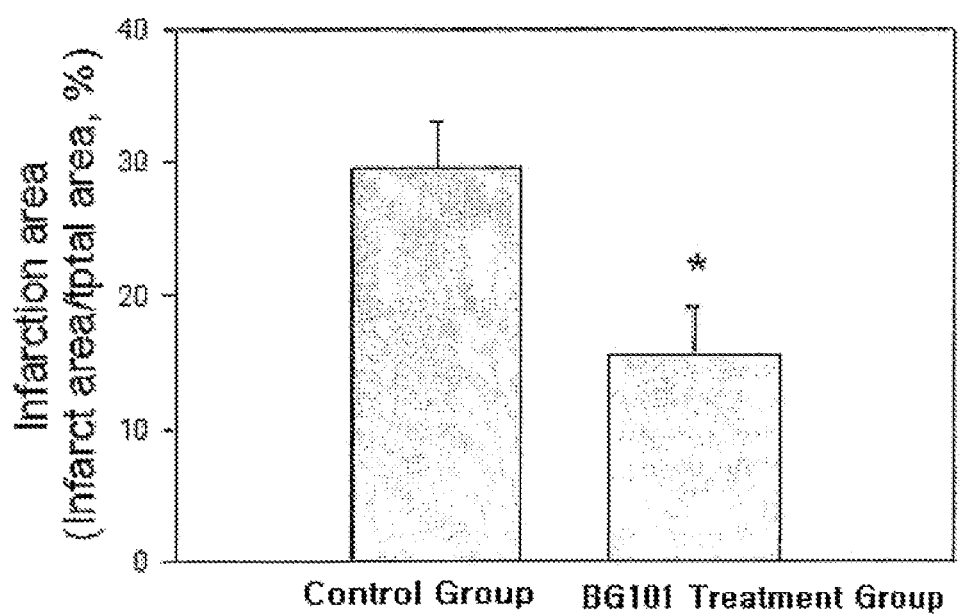
FIG. 11 is a graph showing the effect of silk peptide herein on parts of ischemic cerebral infarction.

As shown in FIG. 9, silk peptide herein decreases the area of infarction region to the level that statistical significance might be acknowledged (P<0.05). The effect of decreased infarction was found throughout the brain (FIG. 10). Further, the volume ratio of infarction region to total brain was also verified to be decreased by pretreatment of BG1-1, as set forth in FIGS. 10 & 11 (average±standard deviation).

Figure 12:
FIG. 12 is a graph showing the effect of silk peptide herein on parts of ischemic cerebral infarction.
Figure 12:
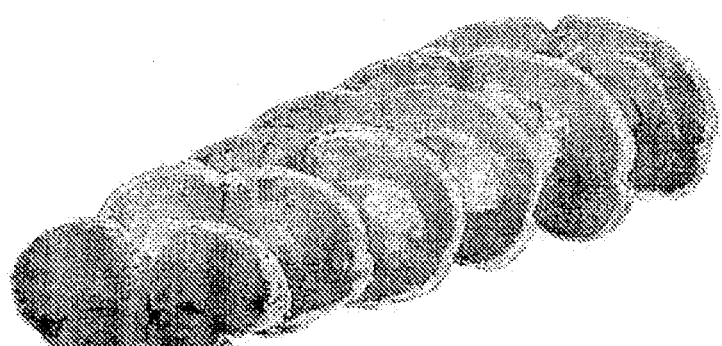

Furthermore, as illustrated in FIG. 12, the region where ischemic infarction was also verified to be decreased when silk peptide herein was treated after the ischemic infarction, was induced.

Therefore, silk peptide was verified to have activity of preventing and treating ischemic stroke and be useful in functional food or drugs of that purpose.

Experimental Example II-2: Local Ischemic Reperfusion Induced Animal Model

A. Medicine Treatment and Preparation of Local Ischemic Reperfusion Induced Animal Model Male Sprague-Dawley rat (200-250 g) was administered with 30-40 mg/kg of ketamine by intramuscular injection, and anaesthetized. Common carotid artery, external carotid artery and internal carotid artery were separated. Superior parathyroid gland and posterior fossa, which are branches of the external carotid artery, and pterygopalatine, which is branch of the internal carotid artery, were electrocauterized, and the external carotid artery were cut. 4-0 nylon thread was incorporated into the internal carotid artery through the external carotid artery and 10-18 mm of nylon thread was placed within the common carotid artery. Reperfusion was performed by suturing the cut skin and removing the nylon thread 1 hour after recovery from anaesthesia.

1 g/kg of BG101 or BG201 was administered once a day for 7 days from the next day of ischemia-reperfusion. Ischemia control group, administered with the same amount and frequency of a physiological saline solution with normal control group and drug treated group, was used as vehicle control group. Passive avoidance test and 8-arm maze test were performed 7 days after induction of ischemia-reperfusion.

B. Analysis of Learning and Memory

B-1. Passive Avoidance Test

Automated shuttle box (Model PACS-30, Columbus Instruments International Company) was used as test device. The shuttle box was divided into two rooms with the same area (19"L×9"W×10.875"H) by middle door (3"L×2.625"W), and their floors were equipped with current-generating device. Each room might be lighted a 20 W light bulb on hinged plexiglass lid. A white rat might enter a dark room through the door. Noise was control below 60 dB and the test was performed in the dark room. The Dawley rat was initially placed in a lighted room and moved to a dark room when the door was opened. At this time, the door was automatically closed and light was turned off. This test was repeated until the rat moved to the dark room within 20 seconds. 26 hours after the end of this discipline, when the rat enter the dark room, the door was closed and 1 mA of current was generated on a floor of the dark room for 3 seconds. 7 days after induction of local ischemia-reperfusion, this rat was placed in the lighted room, and time required for the rat to move to the dark room was measured. The time was limited to 5 minutes (FIG. 13).

Figure 13:
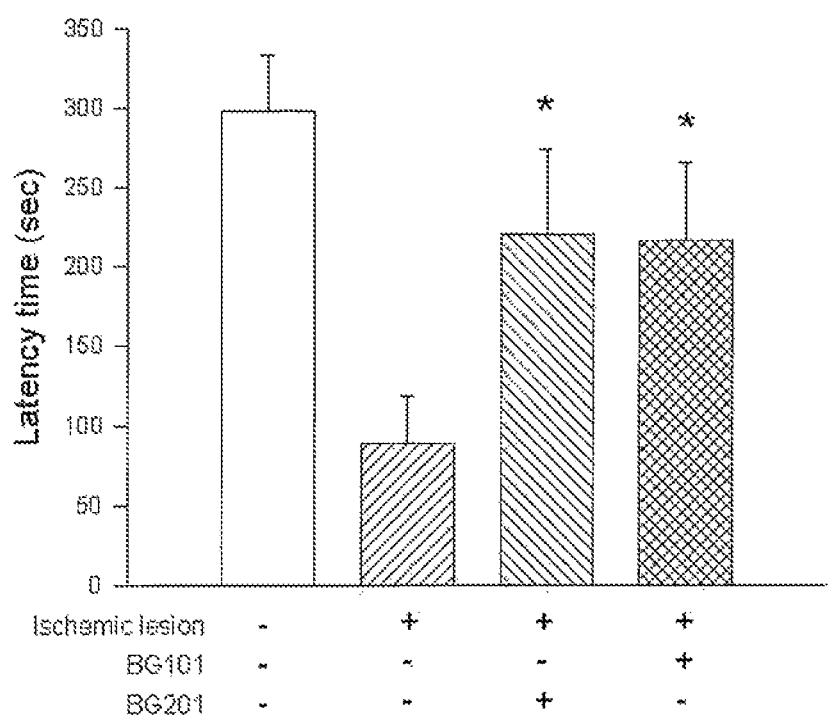
FIG. 13 is a result of passive avoidance test showing that silk peptide here prevents the cerebral damage due to ischemic-reperfusion.

As shown in FIG. 13, latency time is related to impairment and recovery of memory, and the elongation of the latency time means improvement of memory. The latency time was not varied with sham operated control group, while it was significantly decreased with ischemia control group which was administered with solvent only (p<0.05) Meanwhile, latency time was verified to be recovered significantly into normal condition in case of BG101 or BG201 treated group (P<0.05). Especially, BG101 was found to be more efficacious because it caused more effective recovery of latency time than BG101.

B-2. 8-Arm Radial Maze Test 8-arm radial maze (Etho Vision, Netherlands) was used as a test device. It was 45 cm above from the bottom, wherein eight arms (60 cm of length and 12 cm of width) are protruded out of the octagonal center (radius: 34 cm) and the arms and the central part consist of walls (45 cm height). Feed cup was placed on end of each arm. Sunflower seeds were used as reward. Darkness was maintained around the maze by using a 50 W light bulb, and the maze was monitored with video camera. Learning test was performed after decreasing feeds to 80% for 1 week. Male rat was left in maze 3 times a day for 3 days for discipline, and frequency and time of visiting arms were measured until the rat ate all the seeds. The discipline was continued until the number of error reached below 2 times within 2 minutes. Entering the already-visited arms again was considered as an error.

Ischemia animal model was prepared by using the disciplined female rat as follows. The rat was administered with 1 g/kg of BG101 or BG201 once a day for 7 days, and the number of error and latency time was compared to those of control group.

Figure 14:
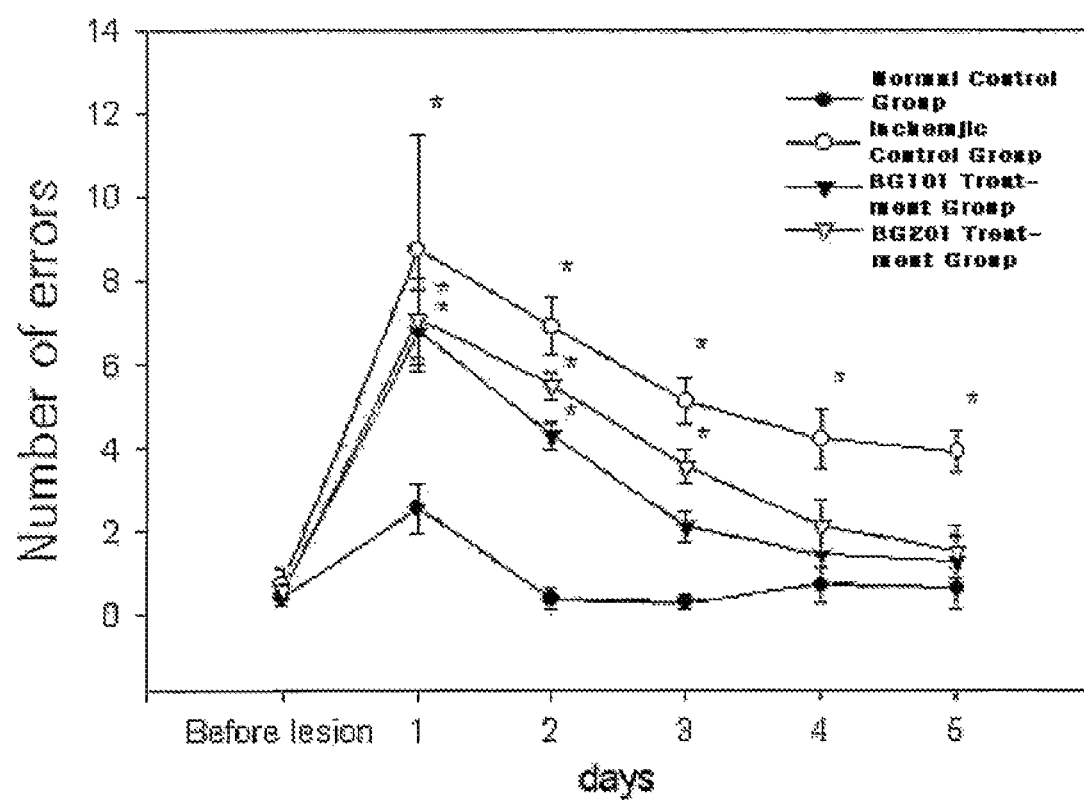
FIG. 14 is a result of 8-arm radial maze test showing that silk peptide here prevents the cerebral damage due to ischemic-reperfusion.

8-arm maze test was performed by using ischemia animal model prepared by stopping, middle cerebral artery (MCA), to verify the activity of BG101 or BG201 on spatial memory that cannot be confirmed by passive avoidance test. Test was performed for 5 days from a week after administration, and the control group did not show any improvement between before and after operation (FIG. 14). In the case of BG101 or BG201 treated group, the number of error was significantly reduced from the third day, and especially BG101 treated group show larger decrease. Until the last day, BG101 or BG201 treated group maintained lowered number of error, while the control group treated with only solvent did not show any recovery (*, P<0.05).

The aforementioned results show that temporary obstruction of middle cerebral artery impaired spatial memory, and repeated administration of BG101 or BG201 recovered the impairment of learning and memory ability due to ischemia. Measured values in FIG. 14 refer to mean±standard deviation (SD).

C. Staining of Hematoxylin & Eosin (H&E) in Hippocampus

It has been reported that deterioration of memory and learning ability due to cerebral ischemia is related to impairment of hippocampus (Hodges et al., Neuroscience, 72(4), 959-88, 1996). Thus, activity of the present invention was measured in certain regions of hippocampus (CA1, CA2, DG).

C-1. Preparation of Tissue

Test animal experiencing the Experimental Example II-2B was anaesthetized with 400 mg/mL of chloral hydrate, and 200 mL of 0.1 M phosphoric acid buffer solution (PBS, pH 7.4) was perfused through heart, thus removing blood component in blood vessel, followed by reperfusion of 250-300 mL of fixing solution (4% paraformaldehyde/PBS). Brain was dissected and post-fixed with the fixing solution at 4° C. for 15-24 hours. After washing the fixing solution with PBS, 10%, 20% and 30% sucrose solutions were incorporated in this order, thus preventing ice crystal. Brain tissue was embedded with embedding solution and quick-frozen in isopentane prefrozen with liquid nitrogen. The continuous coronal slicing of brain tissue was performed into 10 μm thickness by using microtoming device (Cryostat; Reichert Frigocut model 2000), immediately attached to slide glass coated with gelatine, dried at room temperature for 1 hour, and placed at −70° C.

C-2. H&E Staining

The slide glass was washed with distilled water and incubated with hematoxylin for 10 minutes. After the reaction, the slide glass was treated with 70% ethanol comprising 1% of HCl, thus removing remnant hematoxylin, and fixed by treating ammonia. The tissue was stained with eosin for 20 seconds and washed with distilled water. It was dried with 70%, 90% and 100% ethanol, respectively, and treated with xylene and sealed with covering glass and Canadian balsam, followed by observation with optical microscope.

C-3. Analyzing Result of H&E Staining

Figure 15:
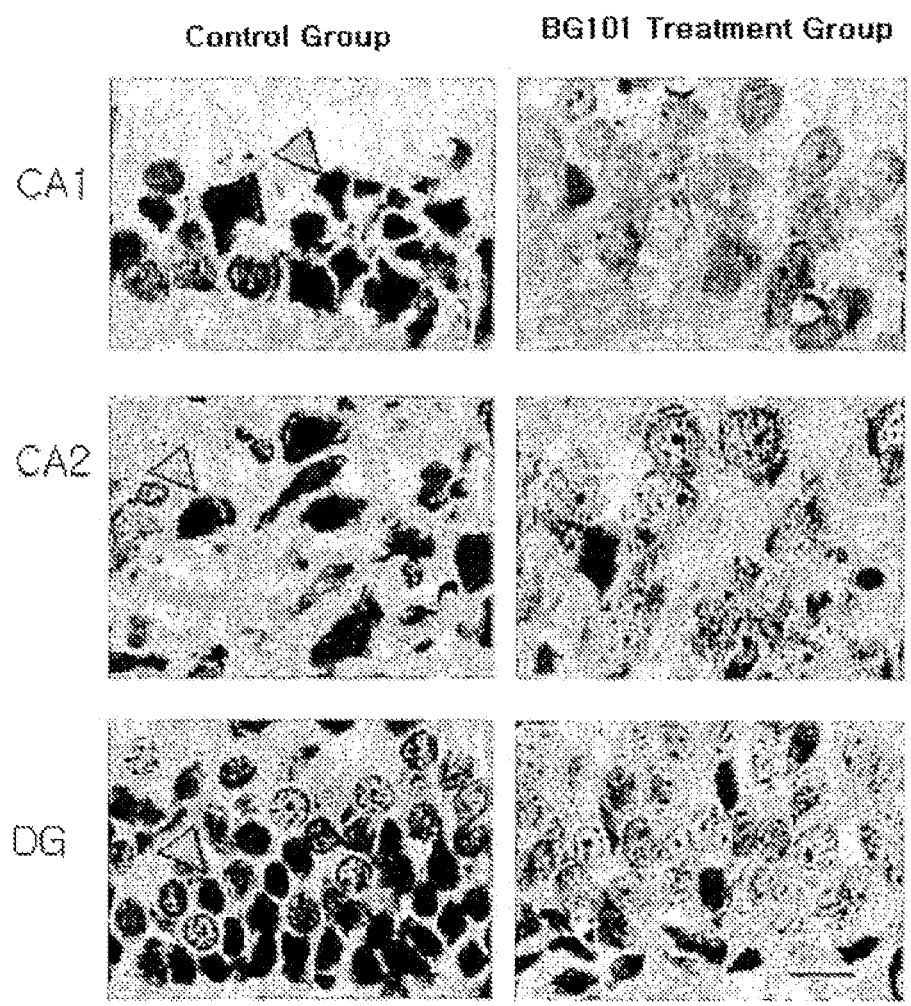
FIG. 15 is a result of H&E dyeing of hippocampus showing that silk peptide here prevents the cerebral damage due to ischemic-reperfusion.

As a result of H&E staining in hippocampus with BG101, in the case of control group induced with ischemia only, eosinophilic phenomenon was found throughout the hippocampus (CA1, CA2, DG), which is typical with cell apoptosis (FIG. 15, arrow). Meanwhile, BG101 treated group showed a significant increase of normal cells.

Although exact mechanism remains to be further studied, BG101 or BG201 is verified to have activity of preventing neuronal apoptosis and cerebral impairment, and be useful in new medicine for treating ischemia.

Experimental Example III: Experiment Using Parkinsonism Animal Model 6-hydroxydopamine (6-OHDA), which is widely used for inducing Parkinson's disease, is absorbed through catecholaminergic neuronal cell membrane and, shows a selective toxic effect on catecholaminergic neuronal cell. Animal model, which was impaired in dopamine neuronal cell by incorporating 6-OHDA in one side brain, is widely used because the other side brain may be used as control group, thus enabling to compare between spontaneous motion and drug-induced rotational motion.

Following experiments were performed to verify the effect of BG101 and BG201 on Parkinson's disease.

Experimental Example III-1: Preparation of Progressive Parkinsonism Animal Model Animal model was prepared by incorporating 6-OHDA in one side striatum of rat and inducing gradual regeneration in dopamine neuronal cells according to Joo's method (Joo W S et al., Neuroreport, 9(18), 4123-4126, 1998) as follows.

Male Sprague-Dawley rats, 8 weeks old (around 200-250 g), which were purchased from Dae Han BioLink Co., Korea), were administered with 3 mL/kg of equithesin by intraperitoneal injection. Skulls of the anaesthetized animals were perforated by using stereotaxic frame (David Kopf, US), and shame group was injected with 0.2 mg/mL of ascorbic acid in their right corpus striatum by using Hamilton syringe (10 μL, 26 G needle) at 1 μL/min, while leisioned group and BG101 or BG210 treated group were injected with dopamine hydroxide (20 μg/5 μL free base in 0.2 mg/mL ascorbic acid) in the same manner (Paxinos et al., J. Neurosci. Methods. 3(2), 129-149, 1980). 5 minutes after drug was injected, the need was withdrawn at a rate of 1 mm/min, and the incision parts were sutured. Meanwhile, BG101 or BG201 was orally administered in two doses of 1 g/kg and 5 g/kg.

In a progressive parkinsonism animal model, the effect of dopamine hydroxide was first confirmed by analyzing behavioral change using apomorphine 14 days after lesion was prepared, and their brains, which were extracted after putting cerbical vertebral out of joint the next day, were used in the experiments. To verify protective effect of BG101 or BG201 on dopamine neuronal cells, lipid peroxidation level, dopamine concentration in corpus striatum by using HPLC and immunohistochemical staining on tyrosine hydroxylase were performed.

Figure 16:
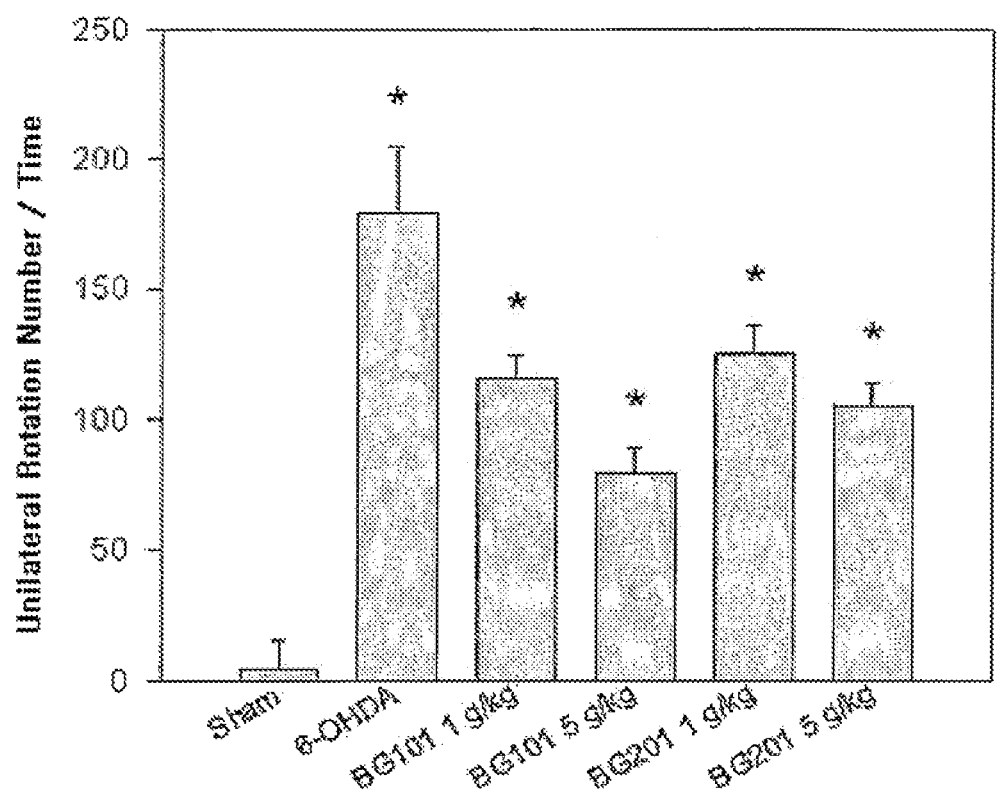
FIG. 16 is a result of unilateral rotation response due to apomorphine by using animal model with Parkinson's disease.

Experimental Example III-2: Unilateral Rotational Response Induced by Apomorphine To verify behavioral change with time in parkinsonism animal model prepared by using dopamine hydroxide, 15 mg/kg of apomorphine was subcutaneously injected in posterior neck 14 days after leision was induced, and unilateral rotational response was measured for 60 minutes (FIG. 16). This experiment uses a principle that, when the concentration of dopamine in corpus striatum was decreased due to death of dopaminic neuronal cells, hypersensitivity of dopamine receptor was induced and apomorphine acts on dopamine receptor as agonist, thus excessively exciting hypersensitivity-induced corpus striatum. As a result, an animal shows a rotational response in the direction opposite to impaired region (Ungerstedt, Brain Res, 24, 485-493, 1970). Rotational response was measured by using automated rotometer referred to in the aforementioned Ungerstedt' journal, and net turns were calculated by using the following formula:

net turns=contralateral turns−ipsilateral turns.

As shown in FIG. 16, normal control group, while administered with 0.2 g/mL of ascorbic acid in corpus striatum, did not show much change in unilateral net turns, leisioninduced control group, administered only with dopamine hydroxide, showed significant increase ($P<0.05$). Meanwhile, target group, administered with silk peptide herein, showed a significant decrease as compared to control group, and the effect was verified to be enlarged as doses increased ($P<0.05$). Each value in FIG. 16 refers to mean±standard deviation.

Experimental Example III-3: Measurement of Amounts of Dopamine and Its Metabolites in Corpus Striatum To verify the effect of BG101 or BG201 on the concentration of dopamine, an important cause of Parkinson's disease, the concentrations of dopamine (DA) and 3,4-dihydroxyphenylacetic acid (DOPAC) were measured in corpus striatum by using HPLC (Gilson, France) 2 weeks after BG101 or BG201 was administered and lesions were incurred, as set forth in the Experimental Example III-2.

A. Preparation of Tissue

Brain of a rat was extracted after putting its cerbical vertebral out of joint, and cut at intervals of 2 mm from optic chiasma by using a brain slicer (ZIVIC MILLER, US), and substantia nigra was separated with tissue punch. Anterior part of the remaining brain was divided into left and right cerebral hemispheres on frozen glass plate. Only corpus striatum was separated and extracted, and rapidly frozen with dry ice and kept at −70° C.

B. Analysis Method

After the frozen test subject was treated with 0.1 M of perchloric acid and 1 mM of EDTA, tissue homogenate was prepared with a sonicator and upper solution was obtained by centrifugal separation at 12,500 g for 20 minutes. The upper solution was filtered onto nitrocellulose membrane filter paper (filter size 0.2 μm) and incorporated into HPLC. WATERS uBondapak™ $C_{18}$ 3.9×300 mm column (particle size 10 μm) was used, and a mixture of 0.07 M sodium phosphate monobasic, 1 mM sodium octanesulfonic acid, 0.1 mM EDTA and 8% acetonitrile (pH 4.0) was used as a mobile phase at a rate of 0.7 mL/min. A predetermined dihydroxybenzylamine had been added to measure the concentration of each material when preparing tissue homogenate as an internal standard material, and separated material was identified by using electrochemical analyzer.

C. Result of HPLC Analysis

Figure 17:
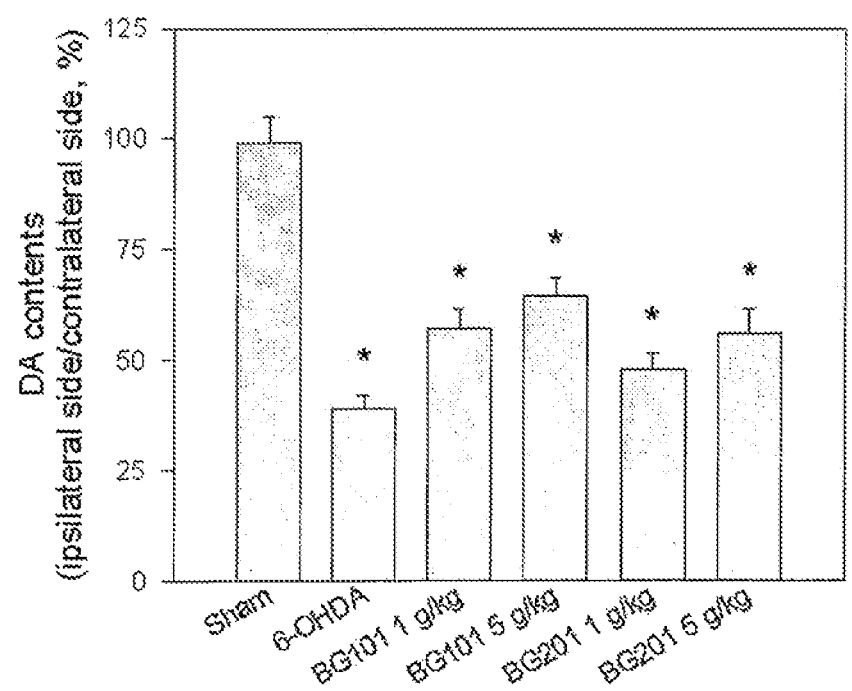
FIG. 17 is a graph showing that silk peptide herein has a neuroprotective activity on dopamine neuronal cell.

As provided in FIG. 17, Dopamine ratio (ipsilateral/contralateral, %) in corpus striatum was significantly decreased in control group treated with only dopamine hydroxide as compared to sham control group (P<0.05). Meanwhile, in silk peptide treated group, the concentration of dopamine increased significantly and in proportion to the dose of administration (P<0.05). Each value in FIG. 17 refers to mean±standard deviation.

Parkinson's disease was incurred when dopamine was decreased in corpus striatum due to destruction of dopamine neuronal cells in substantia nigra. Decrease in concentration of dopamine induced by 6-OHDA is an important sign of destruction of dopamine neuronal cell in substantia nigra and dopamine neuronal fibril ends in corpus striatum. In fact, only about 10% of dopamine remains in corpus striatum in case of patient of last stage of Parkinson's disease as compared to healthy people. Therefore, silk peptide herein was physiologically and biochemically verified to inhibit the decrease of dopamine concentration, and thus have protective activity on dopamine neuronal cell.

Experimental Example III-4: Measurement of Lipid Peroxidation Level in Corpus Striatum (Malondialdehyde Experiment)

To verify how BG101 or BG201 inhibits lipid peroxidation, amount of malondialdehyde (MDA) was measured in corpus striatum 2 weeks after BG101 or BG201 was administered and lesion was prepared as set forth in Experimental Example III-2.

A. Preparation of Tissue

Corpus striatum was extracted according to the aforementioned method, tissue homogenate was prepared by adding Krebs-Ringer Buffer (NaCl 120 mM, KCl 4.8 mM, $CaCl_2$ 1.3 mM, $MgSO_4$ 1.2 mM, $NaHCO_3$ 25 mM, Glucose 6 mM, pH 7.6) and by using a sonicator.

B. Measurement of Lipid Peroxidation

As an index of lipid peroxidation, TBARS (Thiobarbituric acid reactive substances) concentration was measured according to Ohkawa's method (Anal Biochem. 95(2):351-8(1979)). After 8.1% SDS, 20% acetic acid (pH 2.5), 0.8% Thiobarbituric acid (TBA) was added to a predetermined amount of tissue homogenate and BHT (2,6-di-t-butyl-p-cresol, 200 µM) was also added to inhibit self-oxidation, reaction was performed at 100° C. for 30 minutes. After the reactor was placed in ice water to rapidly terminate the reaction, absorption was measured at 532 nm, and TEARS concentration was calculated.

The concentration of MDA-TBA (Malonaldehyde-thiobarbituric acid) complex was measured by using HPLC according to the method of Lazzarino et al. (Lazzarino et al., Free. Radic. Biol. Med. 13(5), 489-98, 1992) and Chirico (1987). The specimen was injected into 5 µM Lichrosper 100 RP18 column (4.6×250 mm), eluted by using 65% $KH_2PO_4$ (50 mM)/15% methanol/20% acetonitrile at a rate of 0.9 mL/min, and detected with UV/visible detector (Hewlett-Packard, Series 1050) by using 1,1,3,3-tetramethoxypropane (prepared in ethanol/water 40:60, v/v) as a standard specimen for indentifying peaks of BG101A-TBA complex.

C. Results

Figure 18:
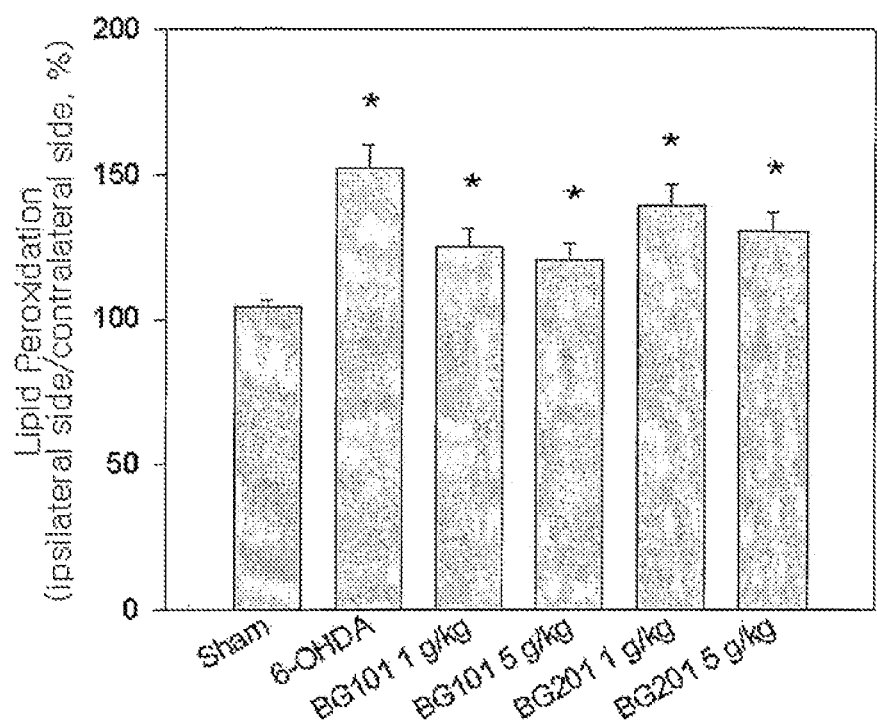
FIG. 18 is a malondialdehyde experiment result showing that silk peptide herein has a remedial efficacy on Parkinson's disease due to its an anti-oxidative function.

MDA generation ratio in corpus striatum (ipsilateral/contralateral, %) was shown as a ratio (%) of concentration of MDA-TBA complex to that of TBARS in FIG. 18. Lipid peroxidation level in corpus striatum significantly increased in case of control group administered only dopamine hydroxide as compared to sham control group (P<0.05). Meanwhile, silk peptide administered group showed significant decrease in lipid peroxidation level as compared to control group, and the degree of decrease was proportion to the administration dose (P<0.05). Each value in FIG. 18 refers to mean±standard deviation.

As the most important cause of aging and degenerative disease, reactive oxygen induces peroxidation of protein and lipid, weakens normal function of cells, and induces oxidative impairment and mutation of DNA. It was recently reported that anti-oxidative enzyme such as glutation peroxidase and catalase is decreased and hydroxyl radical ion is abnormally increase due to the increase of ferrous ion in patients of Parkinson's disease, and it indicates that oxidative stress in an important factor for inducing Parkinson's disease (Ogawa, Eur. Neurol. 34(suppl), 20-28, 1994). Therefore, it may be concluded that silk peptide herein that can decrease lipid peroxidation degree has an activity of suppressing aging process.

Experimental Example III-5: Measurement of Ratio of TH Immuno Positive Cells in Substantia Nigro (TH Immunohistochemical Experiment)

To verify the effect of BG101 or BG201 herein on parkinsonism animal model, TH immunohistochemical experiments were performed. 2 weeks after BG101 or BG201 was administered and leision was prepared as set forth in Experimental Example III-2, TH immunohistochemical staining of substantia nigro slice was performed and the number of stained TH immuno-positive cells was counted by using high-powered microscope.

A. Preparation of Tissue

As explained in Experimental Example II-2, after test animal was administered with BG101 or BG201 and lesion was induced, the test animal was anaesthetized with 400 mg/mL of chloral hydrate, and 200 mL of 0.1 M phosphoric acid buffer solution (PBS, pH 7.4) was reperfused through heart, thus removing blood component in blood vessel, followed by reperfusion of 250-300 mL of fixing solution (4% paraformaldehyde/PBS). Brain was extracted and post-fixed with the fixing solution at 4° C. for 15-24 hours. After washing the fixing solution with PBS, 10%, 20% and 30% sucrose solutions were incorporated in this order, thus preventing ice crystal. Brain tissue was embedded with embedding solution and quick-frozen in isopentane pre-frozen with liquid nitrogen. The continuous coronal slicing of brain tissue was performed into 10 µm thickness slices by using microtoming device (Cryostat; Reichert Frigocut model 2000), and placed in preserving solution comprising 30% glycerol, 30% ethylene glycol and 10% phosphate salt buffer solution (PB).

B. Immunohistochemical Analysis

Tissue was taken out of the preserving solution, washed with PBS 3 times for 10 minutes each time, and reacted with 5% hydrogen peroxide for 10 minutes, followed by reaction with 10% normal goat serum (NGS), 3% BSA (Sigma) and 0.3% Triton X-100 for 30 minutes. It was reacted, in this order, with mouse αTH (dilution ratio=1:500, Boehringer Mannheim) as a first antibody for one day, with biotinylated Vector laboratories (US) as a second antibody for 1 hour at room temperature, and with avidin-biotin-peroxidase composite (ABC, Vector laboratories, US), pre-diluted at a ratio of 1:100 before 30 minutes, at room temperature for 1 hour. The tissue was placed in DAB (diaminobenzidine 0.05%, $H_2O_2$ 0.003%) for 5 minutes for visualization, and was attached to gelatin-coated slide and dried. It was dewatered by using 70%, 90% and 100% ethanol, treated with xylene, sealed with covering glass and Canadian balsam, and observed, with microscope. In the aforementioned culture step, excess reagent was washed with PBS 3 times for 10 minutes each time. Comparative staining was performed by using normal serum instead of first and second antibodies.

C. Result of Immunohistochemical Analysis

Figure 19:
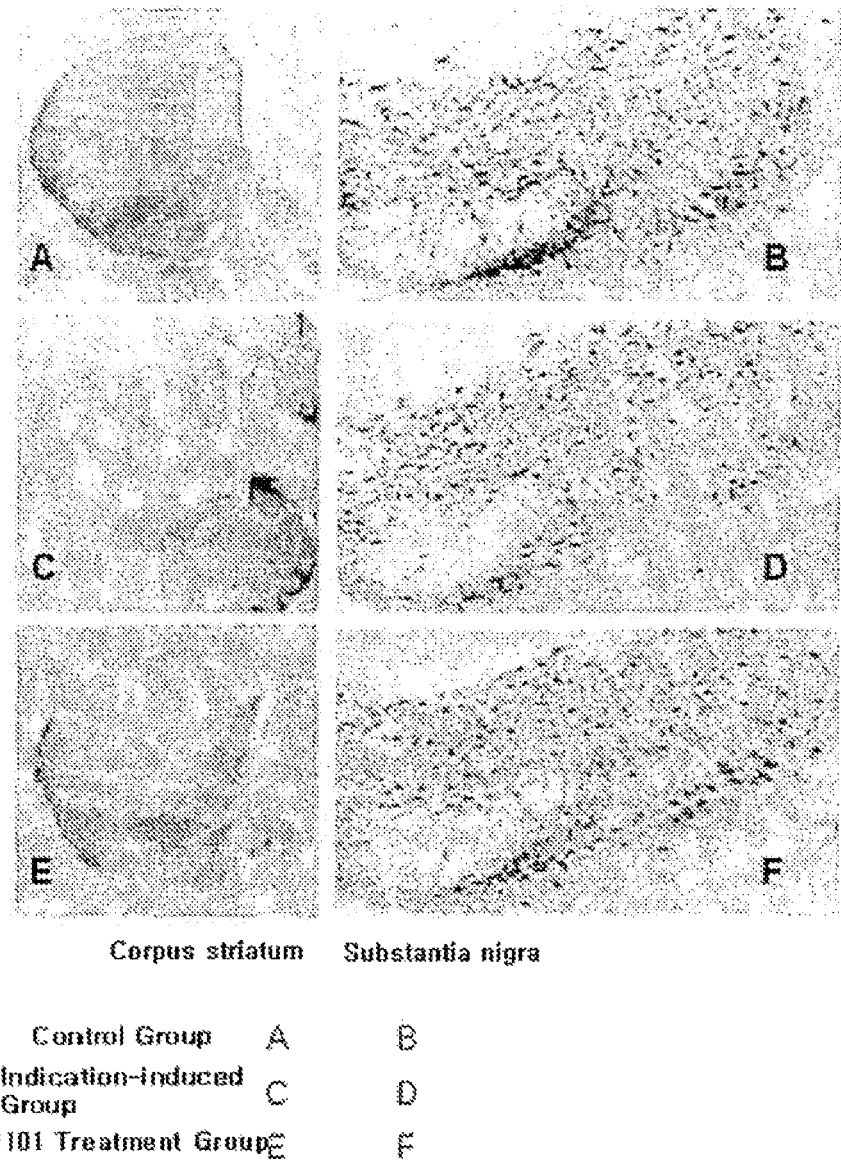
FIG. 19 is a result of tyrosine hydroxylase dyeing experiment showing that silk peptide has a remedial efficacy on Parkinson's disease.
Figure 20:
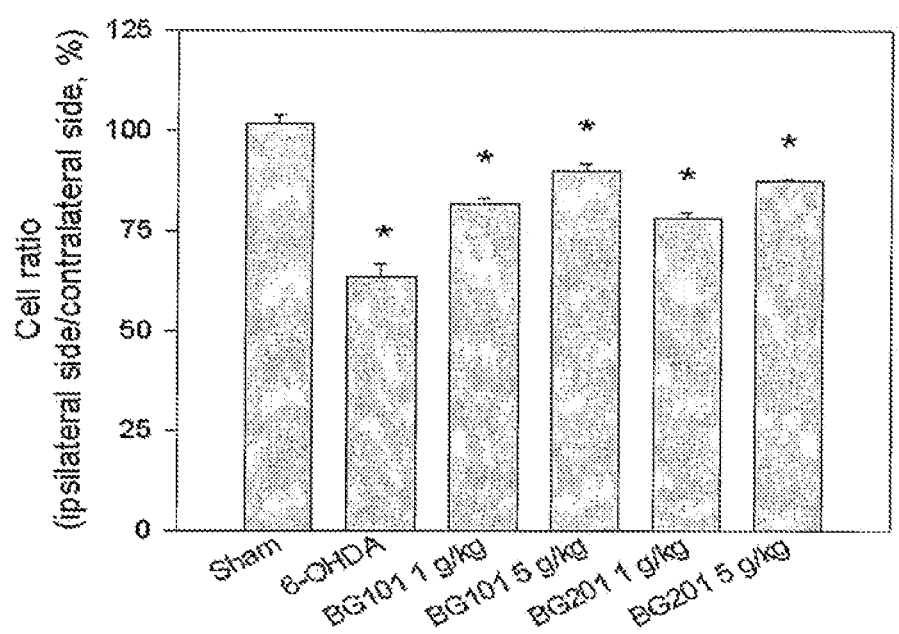
FIG. 20 is a result of tyrosine hydroxylase dyeing experiment showing that silk peptide has a remedial efficacy on Parkinson's disease.

The result of TH immununohistochemical staining with BG101 or BG201 in corpus striatum and substantia nigra and a variance of TH immuno positive cell ratio (ipsilateral/contralateral, %) in substantia nigra were provided in FIGS. 19 and 20, respectively.

As shown in FIG. 19, in normal control group, TH immuno staining in corpus striatum and dopamine neuronal cell in substantia nigra were clearly expressed. In contrast, in lesion control group, corpus striatum was not stained in Doso-lateral area and most of dopamine neuronal cells in substantia nigra par compacta were destroyed. Meanwhile, the group administered with silk peptide herein showed a significantly protective activity on dopamine neuronal fibril ends and neuronal cells as compared to control group.

As shown in FIG. 20, TH immuno positive cells were significantly decreased in leision control group administered only with dopamine hydroxide as compared to normal control group ($P<0.05$). Meanwhile, the group administered with silk peptide herein was verified to significantly increase the TH immuno positive cells and the increase was in proportion to administration dose ($P<0.05$). Each value in FIG. 20 refers to mean±standard deviation.

TH is an essential enzyme in generation of dopamine from tyrosine. TH-stained dopamine neuronal cells and ends may generate dopamine and form dopaminergic neural network. Thus, the aforementioned results show that silk peptide herein has a protective activity for dopamine neuronal cells. Therefore, silk peptide herein may be used in functional food or drug for preventing or treating degenerative cerebral disease, Parkinson's disease.

Experimental Example IV: Effect of Concentration of Acetylcholine

Experiment was performed to verify that BG101 or BG201 herein inhibits the decrease of acetylcholine in brains of rats that was treated with amyloid β, thus serving a function of improving brain activity and inhibiting degenerative cerebral disease.

Experimental Example IV-1: Preparation of Animal Test Subject

Four Sprague Dawley rats (140-180 g, Dae Han BioLink Co., Korea) each box were placed under constant condition (temperature: 25±1° C., relative humidity: 60±10%), and fed with unlimited water and food for 1 week.

Experimental Example IV-2: Measurement of Concentration of Acetylcholine

The concentration of acetylcholine was measured by using chemiluminescence according to methods of Islael and Lesbats (J. Neurochem. 37(6):1475-83(1981)). This method uses reactions that acetylcholine was hydrolyzed into choline by esterase and further changed to bestaine and hydrogen peroxide by choline oxidase. Hydrogen peroxide emits light when chemically reacted with luinol (5-amino-1,2,3,4-tetrahydro-1,4-phthalazinedione; Merck, Darmstadt, Germany) and peroxidase (Sigma, USA), and the amount of emitted light may be used to determine the concentration of acetylcholine.

Figure 21:
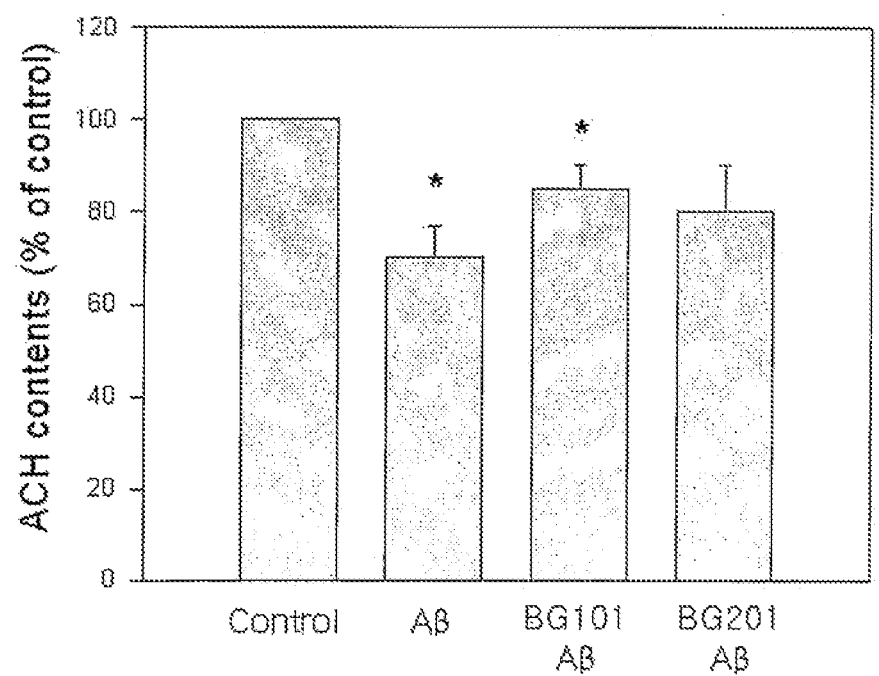
FIG. 21 is a graph showing that silk peptide herein inhibits the decrease in concentration of cerebral acetylcholine.

While Aβ decreased about 75% of acetylcholine in Aβ treated control group as compared to normal control group, the group treated with BG101 or BG201 for 1 week significantly inhibited the decrease of acetylcholine ($P<0.05$). Each value in FIG. 21 refers to mean±standard deviation.

Acetylcholine is neurotransmitter that is projected from basal ganglia to cerebral cortex or hippocampus, thereby performing a very important activity for normal brain function (Richter et. al., *Life Sci.* 19; 26(20):1683-9(1980)). Especially, learning and memory has been known to be varied by drug acting on acetylcholine system. Investigation of people who died of Alzheimer type dementia has showed that their acetylcholinergic neuronal cells are much damaged. Choline agonists and choline esterase inhibitors has been used for patients, as it is recently known that the increase of acetylcholine acts in treating or preventing dementia by improving cognitive function and inhibit the development of dementia. Up to present, there have been developed acetylcholine precursor such as Lecithin; receptor agonist such as RS-86 and nicotine; and acetylcholine esterase inhibitor such as Tacrine and Aricept, the former of which was approved by FDA and is on the Korean market and the latter of which was also recently approved by FDA. However, their use is still open to argument because their effects do not last long and, weak and also seriously toxic.

The aforementioned results showed that silk peptide herein inhibits the decrease of acetylcholine in brain, thus improving brain function and inhibiting degenerative cerebral disease.

Experimental Example V: Depression Animal Model Experiment

Experimental Example V-1: Preparation of Animal Test Subject

Four Sprague Dawley rats (140-180 g, Dae Han BioLink Co., Korea) each box were placed under constant condition (temperature: 25±1° C., relative humidity: 60±10%), and fed with unlimited water and food for 1 week. Fifty rats were selected for experiment among the rats by excluding ones that were undeveloped, show less motion or abnormal behavior in forced swimming test.

Experimental Example V-2: Depression Animal Model Experiment

As a standard method for behavioral despair test, a forced swimming test (FST) was used in this experiment, which is known as principal test for verify anti-depression efficacy. FST test was performed as follows according to its proposer Porsolt et al. (Porsolt et al., Eur. J. Pharmacol. 51(3), 291-294, 1978).

A rat was placed for 15 minutes in a transparent cylindrical water tank with 40 cm of height and 18 cm of diameter, which was filled with 15 cm deep water. Although the rat violently tried to go out of the tank for the first several minutes, the immobilization time increased as time went by, and the rat maintained its body in the immobilization state for the last several minutes. The immobilization state typically refers to a state that a rat pushes only its head above the surface and was in a minimum motion for keeping itself afloat. After forced swimming test, the rat was dried at 37° C. for 30 minutes and returned to the box.

After 24 hours, the second forced swimming was performed for 5 minutes under the same condition with the first forced swimming test, and total immobilization time was measured. Due to learned helplessness, a rat usually shows more immobilization time compared to the first forced swimming test. If a medicine decreases the immobilization time, it may be considered to have an activity related to anti-depression function. Because some medicine loses its functions in a long-term administration in spite of its efficacy in acute treatment and the anti-depression activity may be obtained after at least 2 weeks, the second forced swimming test was performed after 7-day administration of medicine as usually done. The immobilization time was measured by recording total process of the forced swimming and comparing between the control group and the experiment group. Values measured by 3 different analyzers were averaged and used as an analysis data.

A. Administration Method

BG101 or BG201 herein was prepared into 100 mg/mL solution and orally administered. One time urgent administration was performed 1 hour before the second forced swimming, and long-term repeated administration was performed from 30 minutes after the first forced swimming for 7 days.

B. Anti-Depression Effect of One Time Urgent Administration

Figure 22:
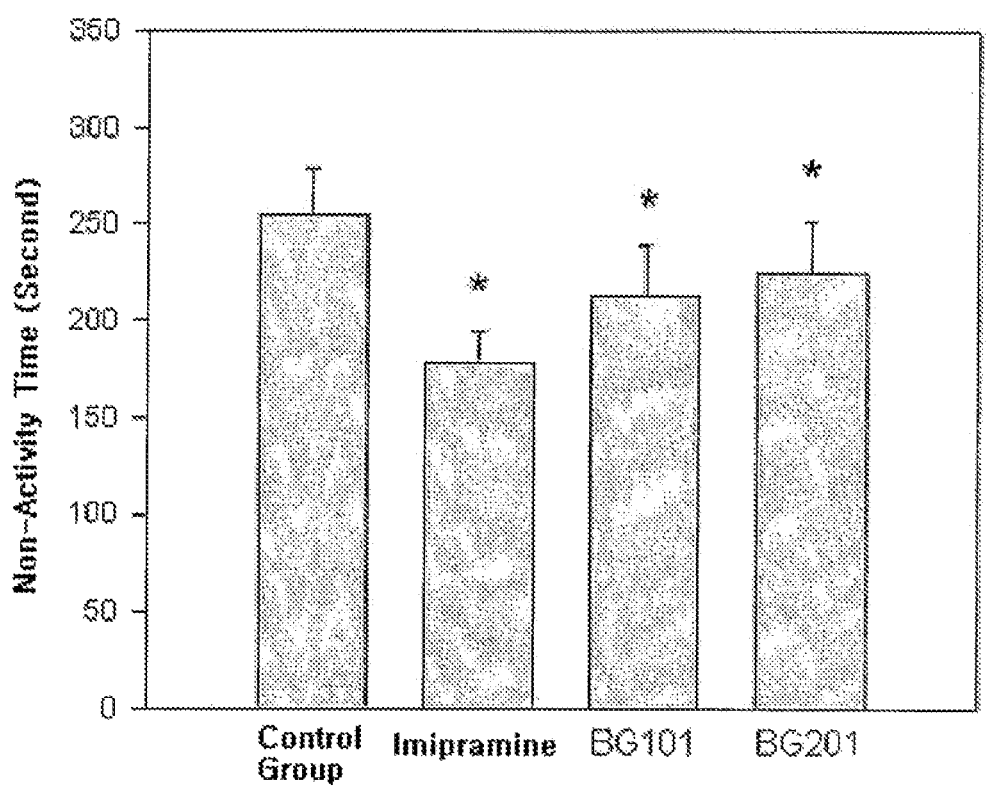
FIG. 22 is a graph showing that silk peptide has an anti-depression activity when administered one time.

Anti-depression effect of one time urgent administration (1 g/kg) was verified. Conventional drug, imipramine (Sigma, US), was used as a positive control group, and dose was determined as 20 mg/kg per administration by referring to research results (Eur. J. Pharmacol. 138(3), 413-416, 1987; Neuropharmacology 28(3), 229-233, 1989). The result was provided in FIG. 22.

Average immobilization time was significantly decreased by imipramine administration compared to control group (*, $P<0.05$). Further, BG101 or BG201 administered group also showed a significant decrease in immobilization time (**, $P<0.05$). Each value in FIG. 22 refers to mean±standard deviation.

C. Anti-Depression Effect of 7-Day Repeated Administration

Figure 23:
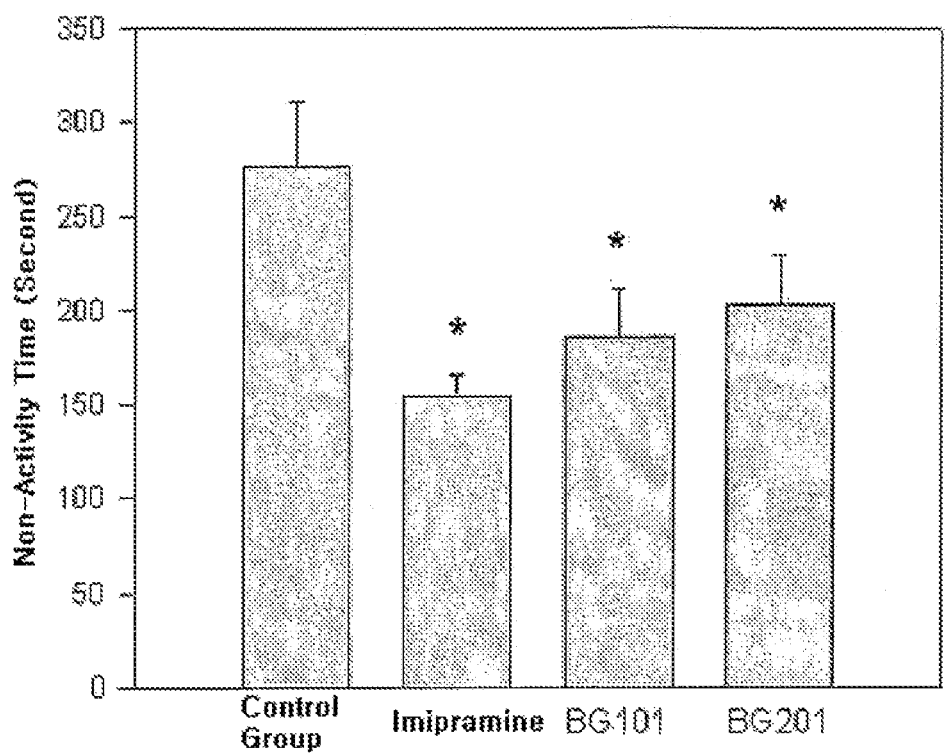
FIG. 23 is a graph showing that silk peptide has an anti-depression activity when administered repeatedly for a long time.

Anti-depression effect of 7-day repeated administration (1 g/kg) was verified. 50 mg/kg of BG101 or BG201 was orally administered one time a day for 7 days, and experiment was performed as aforementioned. The result was provided in FIG. 23.

Average immobilization time was significantly decreased by imipramine administration compared to control group ($P<0.05$). Further, BG101 or BG201 administered group also showed a significant decrease in immobilization time ($P<0.05$), Each value in FIG. 23 refers to mean±standard deviation.

From the results above, it may be verified that imipramine decreased immobilization time as compared to control group, and BG101 or BG201 has also an statistically significant anti-depression activity although it is lower than that of imipramine. However, considering side effect of imipramine when administered long time, BG101 or BG201 has an advantage that it may be administered in large amount for long time and thus may have superiority in preventing or treating depression.

Experimental Example VI: Clinical Test for Improvement of Brain Function

Clinical test subjects were divided into two groups: (i) 67 of test group intaking capsule comprising 100 mg of BG-101 herein ("BF-7") (33 of BF-7 200 mg/day group & 34 of 400 mg/day group), (ii) 32 of placebo group, and took capsules twice a day for 3 weeks.

Rey-Kim test was performed before and 3 weeks after intaking capsules, and the change was evaluated.

Rey-Kim test consists of Auditory Verbal Learning Test (AVLT) and Complex Figure test (CFT).

A. AVLT (1) Repeated Test

After words were mentioned each a second, test subject was required to recall the words, and test was repeated totally 5 times, (2) Delayed Recall After delayed period of 20 minutes, the test subject was required to recall the words again.

(3) Delayed Conformation

After delayed recall test, the subject test was given a paper and required to circle only the mentioned words.

B. CFT (1) Drawing Test

A test subject was given CFT figures and a response paper before test, and required to draw the figures. After drawing, the CFT figures and the paper were laid aside so that the test subject may not see them.

(2) Immediate Recall Test

The subject test was required to draw the figures immediately after the drawing test.

(3) Delayed Recall Test

After delayed period of 20 minutes, the test subject was required to draw the figures again.

(4) Evaluation of CFT

Each of 18 items was evaluated considering its shape and place as from zero to 2 points according to CFT evaluation standard. Thus, each test may get from zero to 36 points.

C. Evaluation Item

① Memory quotient (MQ): the most direct reflective index of memorizing ability.

② Memory maintenance: an index indicating how much and how well memory is maintained precisely ③ Recall efficiency: an index indicating how precisely and efficiently memory is utilized ④ Drawing/memory consensus: an index for determining whether an improved drawing result was caused by a drawing ability or memory ⑤ Intelligence/memory consensus: an index indicating a relationship between enhancement of intelligence and enhancement of memory D. Statistic Analysis of Data The paired t-test was used to analyze difference between scores before and after administration. ANOVA was used to determine whether the differences of scores between the placebo, BF-7 200 mg, and BF-7 400 mg groups has statistical significance or not.

E. Result (1) Improvement of MQ by BF-7

Figure 24:
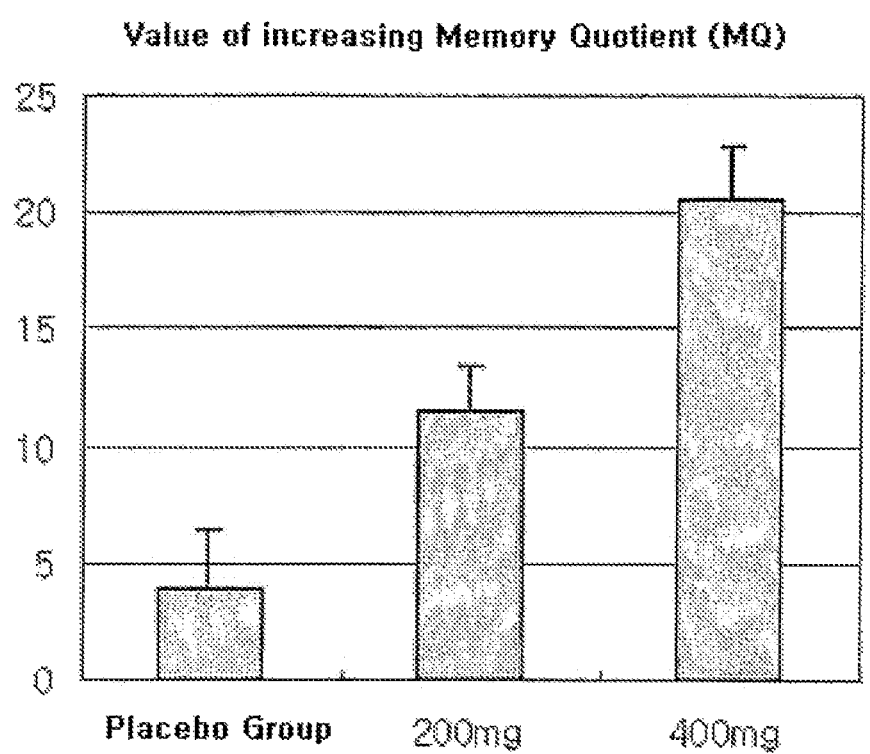
FIGS. 24 and 25 are graphs showing that BF-7, a capsule comprising silk peptide herein has an effect of increasing memory quotient (MQ).
Figure 25:
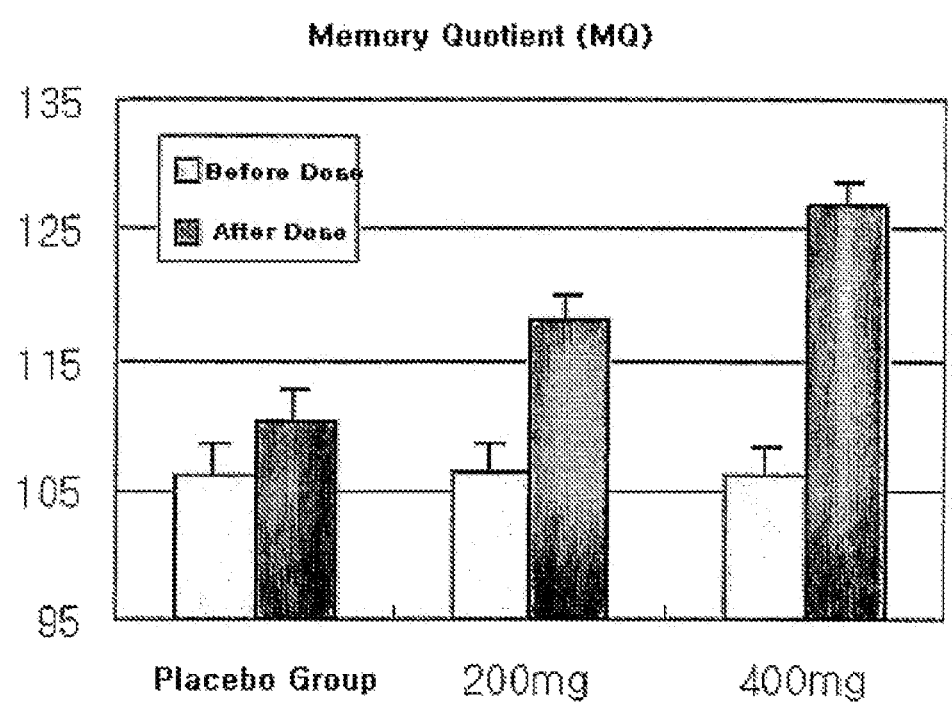

Differences between MQ's before and after administration of the placebo, BF-7 200 mg and BF-7 400 mg groups are 3.1, 11.6 and 20.6, respectively. This result showed that the three cases all showed significant improvement and that the improvement was in proportion to BF-7 dose (FIG. 24). MQ's were improved from 106 to 110, from 106.5 to 118, and from 106 to 126 in the cases of the placebo, BF-7 200 mg and BF-7 400 mg groups, respectively (FIG. 25).

(2) Improvement of Recall Efficiency by BF-7

Figure 26:
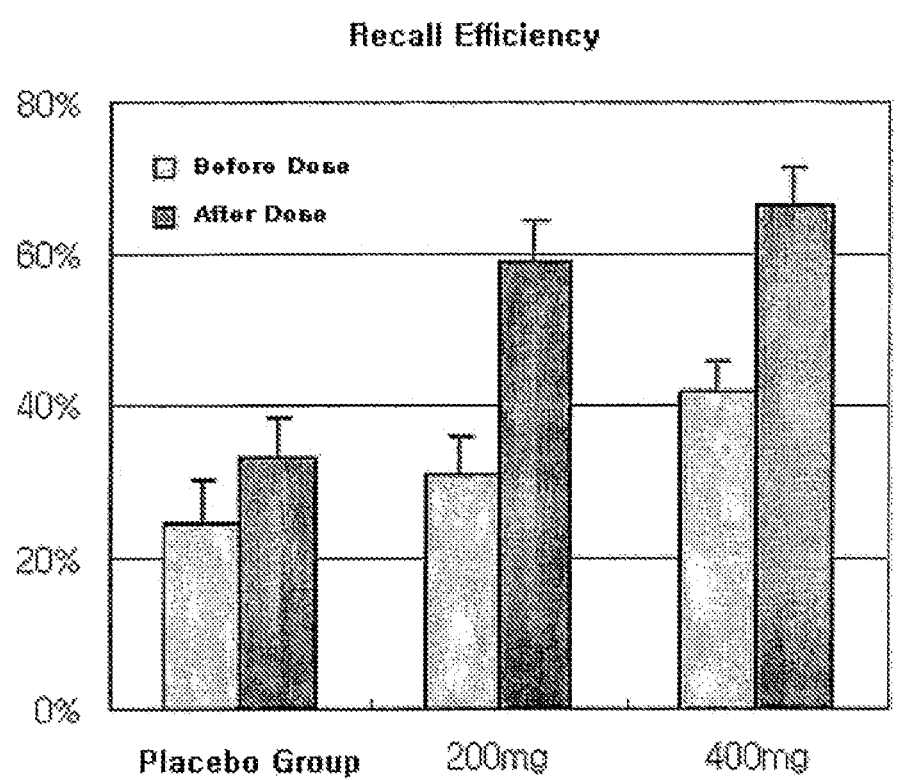
FIG. 26 is a graph showing BF-7, a capsule comprising silk peptide herein has an effect of improving recall efficiency.

A higher percentage score means better recall efficiency. While the placebo group showed no significant improvement, BF-7 200 mg and BF-7 400 mg groups showed significant improvement from 31% to 58.9% and from 41.5% to 66.5%, respectively (FIG. 26).

(3) Improvement of Drawing/Memory Consensus by BF-7

Figure 27:
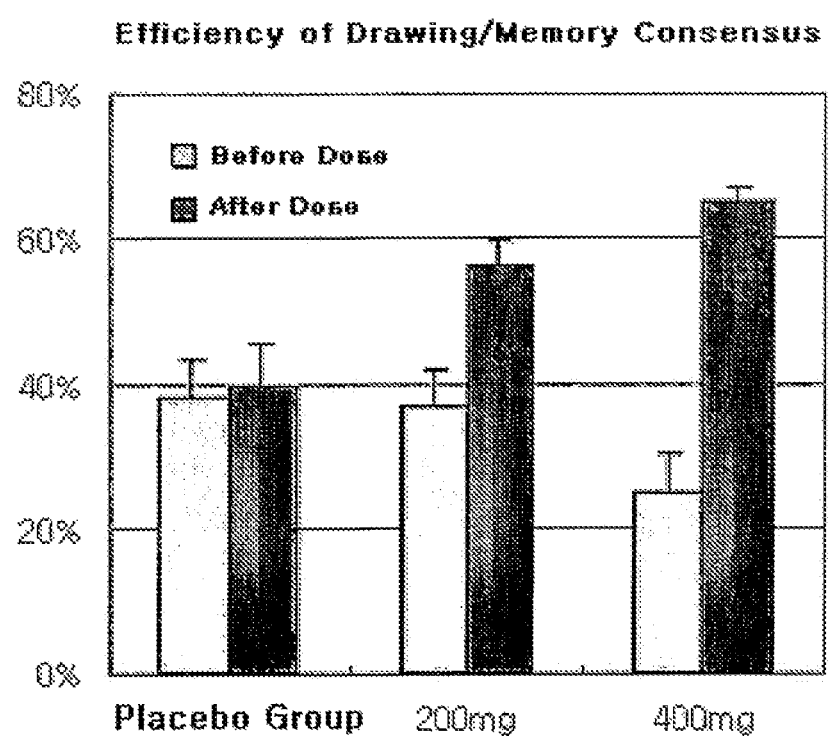
FIG. 27 is a graph showing BF-7, a capsule comprising silk peptide herein has an effect of improving drawing/memory consensus.

As a percentage score is lower, a drawing result is more ascribed to lowered memory. While the placebo group showed no significant improvement from 38% to 40% (P>0.05), BF-7 200 mg and BF-7 400 mg groups showed significant improvement from 36.8% to 56.5% and from 24.7% to 65.2%, respectively, which showed that an improvement of intelligence is not ascribed to drawing ability improvement but memory improvement (FIG. 27).

(4) Improvement of Intelligence/Memory Consensus by BF-7

Figure 28:
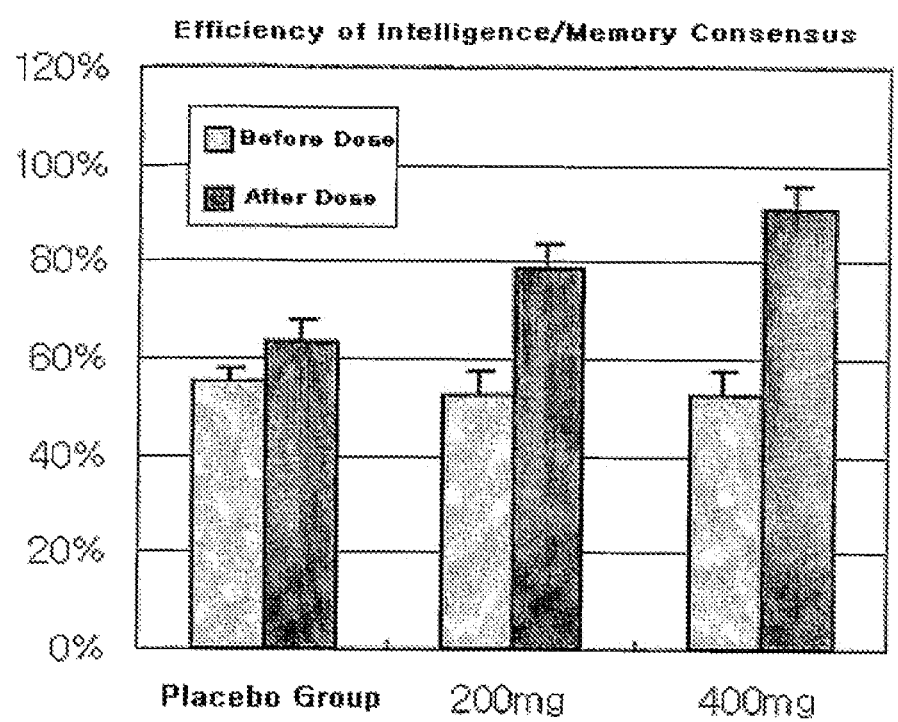
FIG. 28 is a graph showing BF-7, a capsule comprising silk peptide herein has an effect of improving intelligence/memory consensus.

A higher percentage score means a better memory among people of same age with similar intelligence. As shown in FIG. 28, the placebo and BF-7 200 mg groups showed significant improvement from 55.5% to 63.4% and 52.9% to 78.9%, respectively. BF-7 400 group showed remarkable enhancement from 52.5% to 91.9% (P<0.05).

(5) Improvement of Memory Maintenance by BF-7

Figure 29:
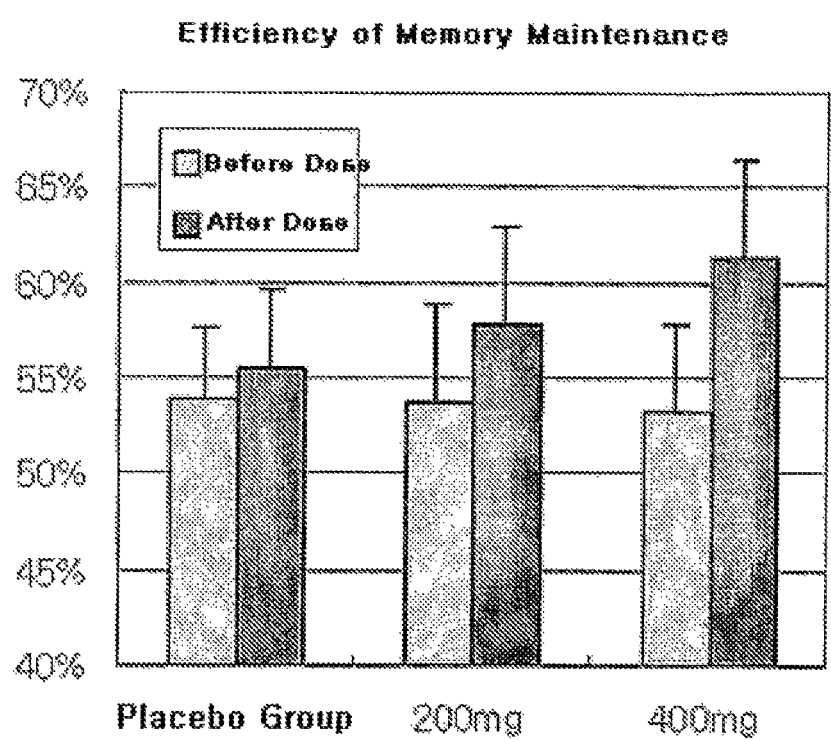
FIG. 29 is a graph showing BF-7, a capsule comprising silk peptide herein has an effect of improving intelligence/memory consensus.

A higher percentage score means better memory maintenance. While the placebo and BF-7 200 mg groups showed no significant improvement (P>0.05), BF-7 400 mg group showed significant improvement from 53.2% to 61.3% (FIG. 29).

As set forth above, from the differences between MQ's before and after administration, it may be verified that all the three cases, the placebo, BF-7 200 mg and BF-7 400 mg groups, showed significant improvement of intelligence. Although the improvement in the placebo group may be ascribed to wide range of standard deviation and, to some extent, a mental effect, as already reported, it can be concluded that BF-7 has an activity of improving intelligence.

Further, from the fact that BF-7 also enhanced other index such as recall efficiency and drawing/memory consensus, it may also conclude that BF-7 helps to improve recall ability, memory and learning ability and effectively acts on neuronal degenerative disease such as dementia, thus being very invaluable material having a lot of scientific and industrial uses.

As described above, the present invention provides a method of efficiently preparing silk peptide having neuroprotective activity and low molecular weight that can facilitates body's absorption.

Further, the present invention provides a composition comprising silk peptide so produced for preventing or treating brain disease or improving brain function. The composition of the present invention shows activities or effects as set forth in Detailed Description and has much lower side effect to human body because it comprises natural material, silk peptide, as an active ingredient.

What is claimed is:

1. A method for improving a brain function of memory and learning ability, comprising
administering to a subject in need of improving memory and learning ability a food composition comprising a silk peptide having an average molecular weight of 850-1,200 determined by gel filtration chromatography as an active ingredient;
wherein the silk peptide is BG101 or BG201, and
wherein the silk peptide is made from *Bombyx mori*.

2. A method for treating Parkinson's disease or depression, which comprises administering to a subject suffering from Parkinson's disease or depression a pharmaceutical composition comprising a silk peptide having an average molecular weight of 850-1,200 determined by gel filtration chromatography as an active ingredient;
wherein the silk peptide is BG101 or BG201, and
wherein the silk peptide is made from *Bombyx mori*.

* * * * *